(12) United States Patent
McKee et al.

(10) Patent No.: US 11,690,789 B2
(45) Date of Patent: Jul. 4, 2023

(54) MULTIPLE-FILL/CHAMBER SOFTGEL DIE

(71) Applicant: R.P. Scherer Technologies, LLC, Las Vegas, NV (US)

(72) Inventors: Shawn P. McKee, Seminole, FL (US); David G. Williams, Sr., Palm Harbor, FL (US); Lester David Fulper, Clearwater, FL (US)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 259 days.

(21) Appl. No.: 16/468,844

(22) PCT Filed: Dec. 22, 2017

(86) PCT No.: PCT/US2017/068103
§ 371 (c)(1),
(2) Date: Jun. 12, 2019

(87) PCT Pub. No.: WO2018/119353
PCT Pub. Date: Jun. 28, 2018

(65) Prior Publication Data
US 2020/0069523 A1 Mar. 5, 2020

Related U.S. Application Data

(60) Provisional application No. 62/438,808, filed on Dec. 23, 2016.

(51) Int. Cl.
*A61J 3/07* (2006.01)
*A61K 9/48* (2006.01)

(52) U.S. Cl.
CPC .............. *A61J 3/07* (2013.01); *A61K 9/4808* (2013.01)

(58) Field of Classification Search
CPC ........... A61J 3/07; A61J 3/077; A61K 9/4808; A61K 9/48; Y10S 53/90
See application file for complete search history.

(56) References Cited

U.S. PATENT DOCUMENTS

| 1,077,835 A | 11/1913 | Kelly |
| 1,356,544 A | 10/1920 | Miller |
| (Continued) | | |

FOREIGN PATENT DOCUMENTS

| CH | 256695 A | 8/1948 |
| CN | 1090483 A | 8/1994 |
| (Continued) | | |

OTHER PUBLICATIONS

Second Office Action for corresponding Israeli application No. 266711; dated Jan. 4, 2022 (3 pages).

(Continued)

*Primary Examiner* — Aradhana Sasan
(74) *Attorney, Agent, or Firm* — Mendelsohn Dunleavy, P.C.

(57) ABSTRACT

The invention provides a die suitable for producing a multi-chamber softgel capsule. The die comprises a die pocket defined by a die pocket wall and a bottom surface. The die comprises one or more partitioning walls dividing the die pocket into two or more chambers The top of the land of the partitioning walls have a lowest point that is lower than the plane formed by the top of the land along the perimeter of the die pocket wall by a gap. A die roll comprising a plurality of the dies is also provided, as well as rotary-die encapsulation machine comprising the die roll.

25 Claims, 14 Drawing Sheets

(56) References Cited

U.S. PATENT DOCUMENTS

| | | | |
|---|---|---|---|
| 1,970,396 | A | 8/1934 | Scherer |
| 2,099,402 | A | 11/1937 | Keller |
| 2,219,578 | A | 10/1940 | Pittenger |
| 2,288,327 | A | 6/1942 | Scherer |
| 2,318,718 | A | 5/1943 | Scherer |
| 2,333,433 | A | 11/1943 | Mabbs |
| 2,340,037 | A | 1/1944 | Zipper |
| 2,355,329 | A | 8/1944 | Ravenscroft et al. |
| 2,497,212 | A | 2/1950 | Donofrio |
| 4,935,243 | A | 6/1990 | Borkan et al. |
| 5,063,057 | A | 11/1991 | Spellman et al. |
| 5,270,054 | A | 12/1993 | Bertolini |
| 5,353,712 | A | 10/1994 | Olson |
| 6,210,107 | B1 | 4/2001 | Volden et al. |
| 6,238,616 | B1 | 5/2001 | Ishikawa et al. |
| 6,260,332 | B1 | 7/2001 | Takayanagi |
| 6,284,234 | B1 | 9/2001 | Niemiec et al. |
| 6,755,010 | B2 | 6/2004 | Draisey |
| 7,490,456 | B2 | 2/2009 | Draisey et al. |
| 8,062,682 | B2 | 11/2011 | Mandralis et al. |
| 8,361,497 | B2 | 1/2013 | Miller |
| 2001/0006689 | A1 | 7/2001 | Ishikawa et al. |
| 2002/0005233 | A1 | 1/2002 | Schirra et al. |
| 2003/0003070 | A1 | 1/2003 | Eggers et al. |
| 2003/0127760 | A1 | 7/2003 | Schurig et al. |
| 2003/0215585 | A1 | 11/2003 | Bunick |
| 2004/0060258 | A1 | 4/2004 | Stolz |
| 2004/0202636 | A1 | 10/2004 | Kaczvinsky, Jr. et al. |
| 2005/0034428 | A1* | 2/2005 | Davis ............... A61J 3/005 53/454 |
| 2005/0191346 | A1 | 9/2005 | Nowak et al. |
| 2012/0052118 | A1 | 3/2012 | Altamar et al. |
| 2012/0128765 | A1 | 5/2012 | Brocker et al. |
| 2014/0008025 | A1 | 1/2014 | El Glaoui et al. |
| 2014/0348934 | A1 | 11/2014 | Puckett |
| 2016/0120755 | A1 | 5/2016 | Puckett |
| 2017/0239142 | A1 | 8/2017 | Fulper et al. |

FOREIGN PATENT DOCUMENTS

| | | | |
|---|---|---|---|
| CN | 1473742 | A | 2/2004 |
| CN | 201399093 | Y | 2/2010 |
| CN | 201404473 | Y | 2/2010 |
| CN | 102369148 | A | 3/2012 |
| CN | 204106587 | U | 1/2015 |
| CN | 104703518 | A | 6/2015 |
| CN | 205659156 | U | 10/2016 |
| EP | 0211079 | A1 | 2/1987 |
| GB | 1596008 | A | 8/1981 |
| KR | 2000-0048339 | A | 7/2000 |
| RU | 2433943 | C2 | 11/2011 |
| WO | WO9735537 | A1 | 10/1997 |
| WO | WO0027367 | A1 | 5/2000 |
| WO | WO0028976 | A1 | 5/2000 |
| WO | 01/36290 | A1 | 5/2001 |
| WO | 2010091026 | A1 | 8/2010 |
| WO | WO2014016510 | A1 | 1/2014 |
| WO | 2014057094 | A1 | 4/2014 |

OTHER PUBLICATIONS

Extended European Search Report for corresponding European application No. 17884681.2; dated Jul. 27, 2020 (7 pages).
Second Office Action for corresponding Chinese application No. 201780071222.4; dated Nov. 26, 2021 (24 pages) Machine Translation.
First Office Action for corresponding Chinese application No. 201780071222.4; dated Mar. 31, 2021 (33 pages) Machine Translation.
Examination Report for corresponding Russian application No. 2019113384; dated Apr. 2, 2021 (16 pages) Machine Translation.
Search Report and Examiner Opinon for corresponding Brazilian application No. BR112019010874-2; dated Mar. 22, 2022 (8 pages) Machine Translation.
International Search Report and Written Opinion for International Application No. PCT/US2017/068103; dated Apr. 16, 2018.
Examination Report for corresponding Indian application No. 201917019801; dated Aug. 31, 2021 (6 pages).
Notice of Reasons for Refusal for corresponding Japanese application No. 2019-533510; dated Jul. 27, 2021 (4 pages).
Third Office Action for corresponding Chinese application No. 201780071222.4; dated May 17, 2022 (12 pages) Machine Translation.
Office Action for corresponding Vietnamese application No. 1-2019-02821; dated May 23, 2022 (3 pages).
Communication pursuant to Article 94(3) EPC for corresponding European application No. 17884681.2; dated Nov. 9, 2022 (5 pages).
Examination Report No. 1 for corresponding Australian application No. 2017382322; dated Nov. 16, 2022 (4 pages).
Technical Examination Report for corresponding Brazilian application No. BR112019010874-2; dated Nov. 22, 2022 (8 pages) Machine Translation.
Office Action for corresponding Colombian application No. NC2019/0005230; dated Sep. 11, 2020.

* cited by examiner

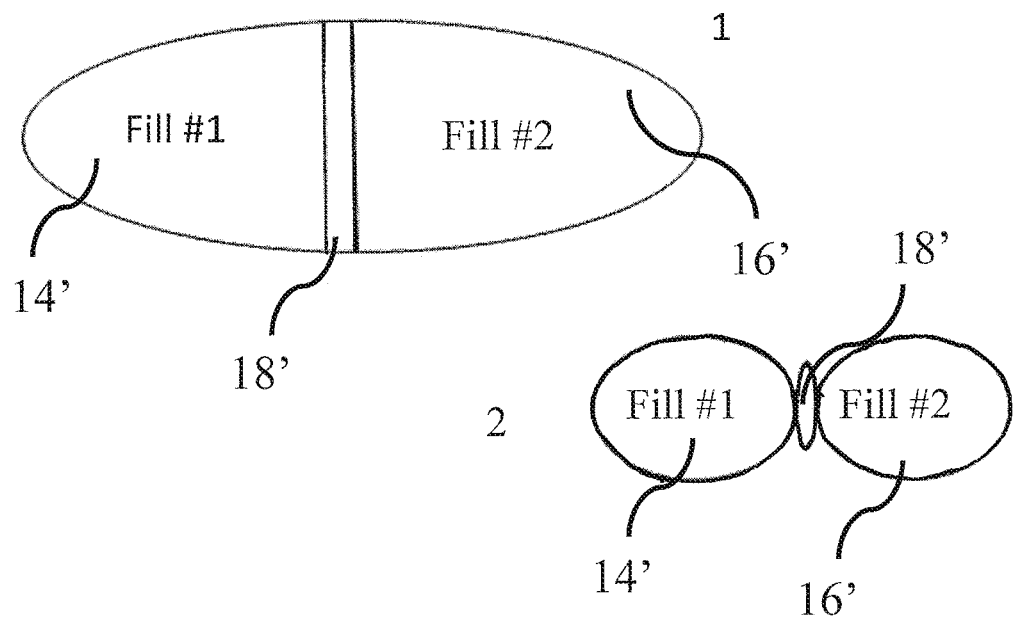
FIG. 19
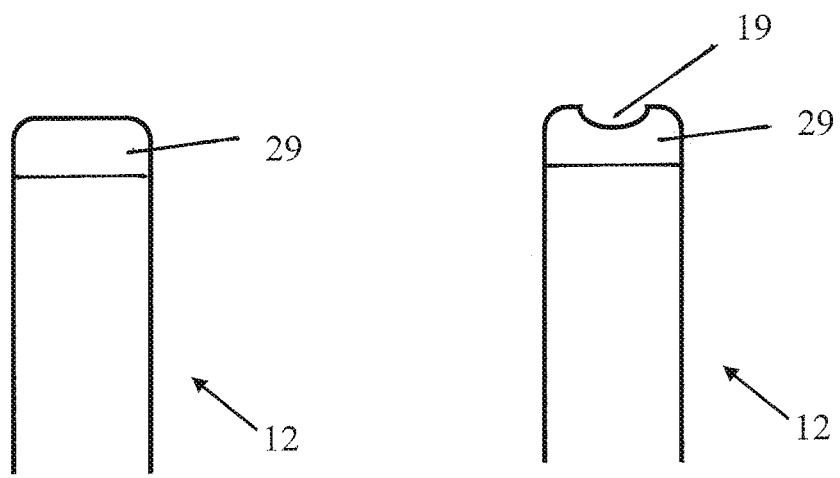
FIG. 20A
FIG. 20B

MULTIPLE-FILL/CHAMBER SOFTGEL DIE

BACKGROUND OF THE INVENTION

1. Field of the Invention

The invention relates generally to a die and process for manufacturing softgel capsules. In particular, the invention relates to a die and process for manufacturing softgel capsules with two or more chambers where each chamber is suitable for encapsulating a different fill material.

2. Description of the Related Technology

In recent years, softgel capsules have become a popular dosage form for therapeutic agents and cosmetic products. The softgel capsules are typically filled with a liquid containing the therapeutic agents or cosmetic substances. In addition, other products such as dietary supplements or veterinary products may also be used in fill materials of the softgel capsules. Because of their soft, elastic character, patients often find these capsules easier to swallow than conventional tablets or hard gelatin capsules. Softgel capsules are also preferred to bulk liquids because they are easier to transport and avoid the need for the patients or users to measure a prescribed amount of the liquid before use.

Softgel capsules are commonly produced by a rotary-die process, which was described in detail in Ebert, W. R., "Soft elastic gelatin capsules: a unique dosage form," Pharmaceutical Tech., October 1977; Stanley, J. P., "Soft Gelatin Capsules," in *The Theory and Practice of Industrial Pharmacy* (Lachman, Lieberman and Kanig, Editors), 3rd Edition, published by Lea & Febiger; and U.S. Pat. Nos. 1,970,396, 2,288,327, and 2,318,718, the teachings of all of which are incorporated herein by reference in their entireties.

A typical rotary-die encapsulation machine for making softgel capsules is illustrated in FIG. 1. There are a plurality of die 5, 5' on the die roll 3, 3'. As the die roll 3, 3 rotating in the directions shown by the arrows in FIG. 1, two gel ribbons 2, 2' are feed into the die roll 3, 3' where the gel ribbons 2, 2' settle into the pockets of die 5, 5'. The settled gel ribbons are brought together on the die roll 3, 3' to form the capsules 1. The fill material is injected into the capsule cavity 7 of the forming capsule 1 through an injection channel 4 of the filling wedge 6. The filled capsules are then pinched off from the remaining of the gel ribbons 2, 2'.

The capsule shell must be compatible with the fill material, especially pharmaceutical agent or cosmetic substance contained in a liquid carrier. In addition to liquids, U.S. Pat. No. 4,935,243 suggests that the fill material may also be a semi-solid, solid, or gel. Conventional tablets or pellets containing an active ingredient are examples of solid fill materials that may be encapsulated within a softgel capsule.

A softgel capsule can contain two or more active ingredients. The ability to encapsulate two or more active ingredients in a single softgel capsule offers several advantages, including convenient delivery of multiple medications/products, avoidance of potential mistakes by user if several medications/products are to be taken at the same time, increased user compliance, achievement of possible synergistic effects and possible controlled delivery. However, in some cases the two or more active ingredients in a softgel capsule can be chemically incompatible. For example, chemical reactions may occur between active ingredients or between an active ingredient and a carrier in the fill material.

Attempts have been made to separate incompatible active ingredients in the same softgel capsule to avoid chemical incompatibilities and to maintain the chemical integrity of the active ingredients. Physical barriers may be utilized in a softgel capsule to separate incompatible active ingredients in different chambers. For example, a partition may be used to divide a softgel capsule into separate chambers with each chamber containing a fill material with a different active ingredient.

EP 0 211 079 A1 discloses multi-chamber softgel capsules and an apparatus for manufacturing the softgel capsules. The multi-chamber softgel capsule consists of at least one partition to divide its inner space into a plurality of chambers. The multi-chamber softgel capsule is manufactured by feeding a first film to form the first covering, a second film to form the second covering, and a third film positioned between the first and second films to form the partition, between a pair of die rolls in a capsule molding apparatus. Separate fill materials are introduced into the space between the partition and the first film and the space between the partition and the second film. These films are then joined by compressing the three films together except at capsule forming portions thereof to form the multi-chamber softgel capsules containing the fill materials.

U.S. Pat. No. 7,490,456 discloses an apparatus for making two-compartment softgel capsules from films of a polymeric material. The apparatus comprises a pair of rotary welding die rolls defining recesses, means to supply the films to the welding die rolls so they are deformed to form recesses, and means to fill the resulting recesses in the films with a fill material, and means to apply high frequency electrical signals between the welding die rolls so the films are welded by dielectric welding to form multi-compartments containing the fill material, and means to cut the filled capsules from the remaining films. The apparatus also comprises a transfer roller and a kiss-cut roller for cutting the filled capsules between the transfer roller and the kiss-cut roller. When three films are supplied to the apparatus where the two outer films form recesses and the middle film forms the divider between the two compartments.

US 2005/0191346 discloses softgel capsules having at least two separate chambers. The softgel capsule includes a dividing wall separating the capsule into two chambers. The dividing wall is formed of two layers of wall material adhered together. An encapsulation apparatus for making such capsules comprises a means for supplying two films to an encapsulation unit, a means for plastically deforming each film to form suitably shaped capsule portions, a means for supplying respective fill material to be encapsulated to the respective capsule portions, a means for supplying a film of dividing wall material to each of the filled capsule portions, and a means for adhering together the capsule portions and dividing wall material to produce a capsule having at least two separate chambers.

U.S. Pat. No. 8,361,497 discloses a multi-compartment capsule. The capsule comprises a first receiving chamber containing at least one ingredient having a first physical state, with the ingredient selected from a nutraceutical, a vitamin, a dietary supplement and a mineral; and a second receiving chamber containing at least another ingredient having a second physical state, with the another ingredient selected from a nutraceutical, a vitamin, a dietary supplement and a mineral. The ingredient in the first receiving chamber is different from the other ingredient in the second receiving chamber. The first physical state in the first receiving chamber is different from the second physical state in the second receiving chamber.

WO 00/28976 discloses softgel capsules having a plurality of chambers separated by barriers. An apparatus for making such softgel capsules comprises a first gel ribbon delivery means for delivering a first gel ribbon between a first wedge and a first roller, second gel ribbon delivery means for delivering a second gel ribbon between a second wedge and a second roller, at least one barrier material delivering means for delivering a barrier material between the first and second wedges where the barrier material forms barriers to divide the capsule into at least two chambers, and an active agent delivering means for delivering at least one active agent to at least one of chambers. The barrier material is substantially non-permeable to any component contained within the chambers.

Making these multi-chamber softgel capsules requires significant modifications of the rotary die encapsulation machines that have been used to make traditional one fill softgel capsules or an extra step in adhering two chambers into a single softgel capsule. These modifications will incur significant cost and an extra adhering step will also incur additional cost to the production process. The present invention provides a new die that can be used in traditional rotary die encapsulation machines with minor modifications for producing multi-chamber softgel capsules without any extra steps. The new die enables efficient production of multi-fill/chamber softgel capsules at a reasonable cost.

SUMMARY OF THE INVENTION

In one embodiment, there is disclosed a die suitable for producing a multi-chamber softgel capsule. The die includes at least:
- a die pocket defined by a die pocket wall and a bottom surface; and
- one or more partitioning walls dividing the die pocket into two or more chambers and wherein the die pocket wall and the one or more partitioning walls have their respective top sections defined as lands,
- a top of the land along the perimeter of the die pocket wall is in a plane, and
- a lowest point of the top of the land of the one or more partitioning walls is lower than
- the plane by a gap.

In each of the foregoing embodiments, the one or more partitioning walls of the die may be perpendicular to the plane comprising the top of the land along the perimeter of the die pocket wall.

In each of the foregoing embodiments, at least one of the lands of the one or more partitioning walls of the die may have a recess in the top.

In each of the foregoing embodiments, the one or more partitioning walls of the die may be, e.g., a straight line or a curved line as viewed from a top view of the die.

In each of the foregoing embodiments, at least one of the one or more partitioning walls may have a thickness decreasing from proximate to the bottom surface of the die to the land of the at least one partitioning wall.

In each of the foregoing embodiments, at least one of the one or more partitioning walls may have a thickness increasing from proximate the bottom surface of the die to the top of the land of the at least one partitioning wall.

In each of the foregoing embodiments, a size of the gap formed between the lowest point of the top of the lands of the one or more partitioning walls and the plane of the top of the land of the die pocket wall may be in a range from about 0.0508 mm (0.002 inch) to about 2.54 mm (0.1 inch), or from about 0.508 mm (0.02 inch) to about 2.032 mm (0.08 inch), or from about 0.508 mm (0.02 inch) to about 1.524 mm (0.05 inch), or from about 0.762 mm (0.03 inch) to about 1.27 mm (0.05 inch).

In each of the foregoing embodiments, the gap may be less than about 95%, or less than about 90%, or less than about 85%, or less than about 80%, or less than about 75%, or less than about 70%, or less than about 65%, or less than about 50%, or less than about 45%, or less than about 40%, or less than about 30%, or less than about 20%, of the thickness of a gel ribbon suitable to be used with the die.

In each of the foregoing embodiments, at least one of the two or more chambers may have a different size than another of the two or more chambers.

In each of the foregoing embodiments, the die may be constructed with one or more high strength materials selected from aluminum, brass, hardened steel, stainless steel, bronze, iron, and die cast zinc.

In each of the foregoing embodiments, the die may be constructed with a high wear-resistance and hot strength alloy selected from alloys based on Co, Ni, or Mo.

In another embodiment, a die roll having a surface comprising a plurality of the dies of any one of the foregoing embodiments is disclosed.

In another embodiment, a rotary-die encapsulation machine comprising at least one die roll that has a plurality of the dies of any one of the foregoing embodiments is disclosed.

In another embodiment, a multi-chamber softgel capsule made using the dies of any one of the foregoing embodiments is disclosed, wherein the multi-chamber softgel capsule has two or more chambers separated by one or more barrier seals.

In the foregoing embodiment, the multi-chamber softgel capsule may have a capsule shell comprising at least one of gelatin, water-soluble cellulose derivatives, seaweed-derived polymers, pectin, polyethylene oxide, polyvinyl alcohol, alginate, polycaprolactone, and gelatinised starch-based materials.

In each of the foregoing embodiments of the multi-chamber capsule, the multi-chamber softgel capsule may encapsulate at least two different fill materials selected from pharmaceutical formulations, dietary supplements, cosmetic products and industrial applications (e.g., two part epoxy systems or two part polyurethane systems).

In each of the foregoing embodiments of the multi-chamber capsule, the multi-chamber softgel capsule may separately encapsulate at least two different materials that, upon use, combine to make a single product.

In another embodiment, a pair of mated dies is disclosed that is suitable for producing a multi-chamber softgel capsule, each of the pair of the dies (10) comprises:
- a die pocket defined by a die pocket wall and a bottom surface; and
- one or more partitioning walls dividing the die pocket into two or more chambers and wherein the die pocket wall and the one or more partitioning walls have their respective top sections defined as lands, the partitioning walls of the pair of mated dies have heights such that there is a gap between the land(s) of the one or more partitioning walls of one of the dies and the land(s) of the one or more partitioning walls of the other die.

BRIEF DESCRIPTION OF THE DRAWINGS OF CERTAIN EMBODIMENT(S)

FIG. 19 shows two alternative multi-fill softgel capsules which may be produced by the die according to some embodiments of the present invention.

FIGS. 20A-20B are cross-section side views of die pocket walls with a top section thereof called the land. The land can have a smooth top surface (FIG. 20A) or a crescent-shaped recess in its top surface (FIG. 20B).

DETAILED DESCRIPTION OF CERTAIN EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

It is to be understood that each feature, component, compound, substituent, or parameter disclosed herein is to be interpreted as being disclosed for use alone or in combination with one or more of each and every other feature, component, compound, substituent, or parameter disclosed herein.

Figure 1:
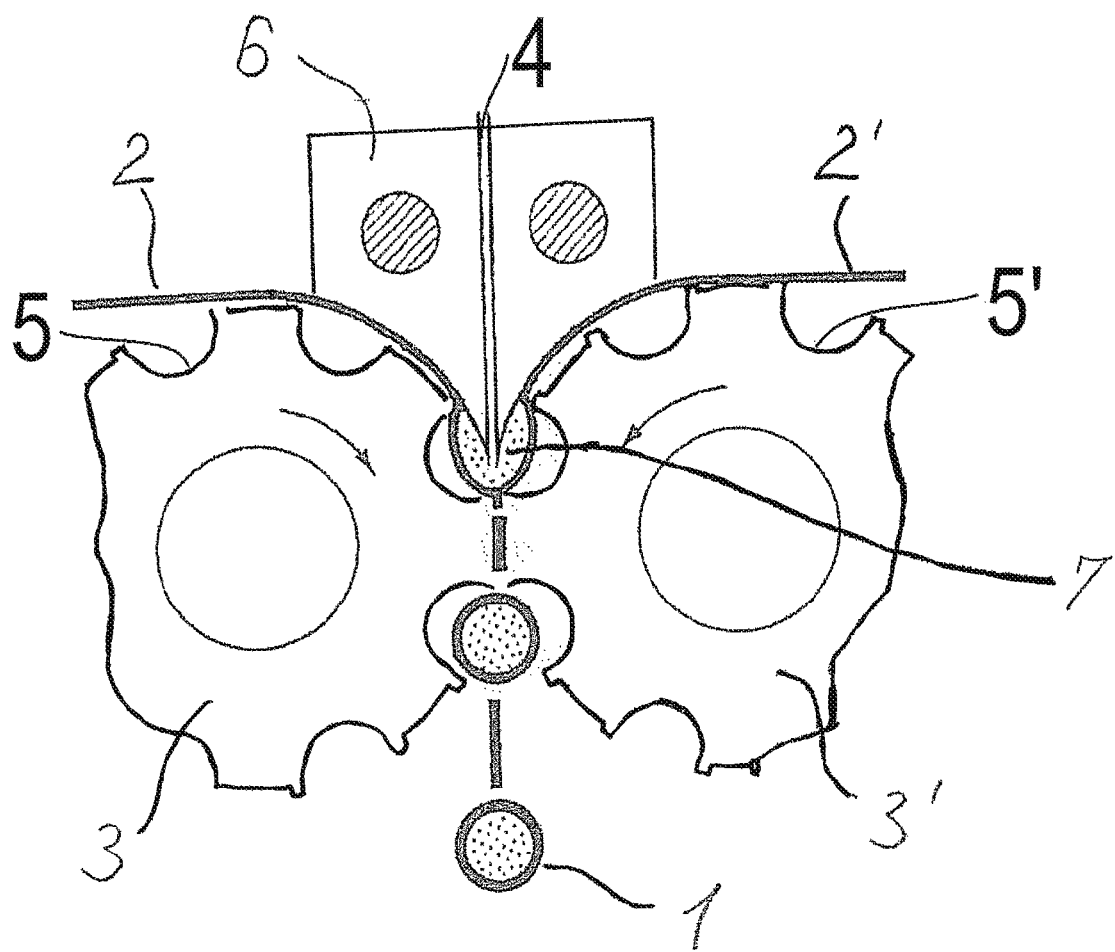
FIG. 1 is a prior-art rotary die encapsulation machine typically used in a conventional rotary-die process to make a single-fill softgel capsule.
Figure 2:
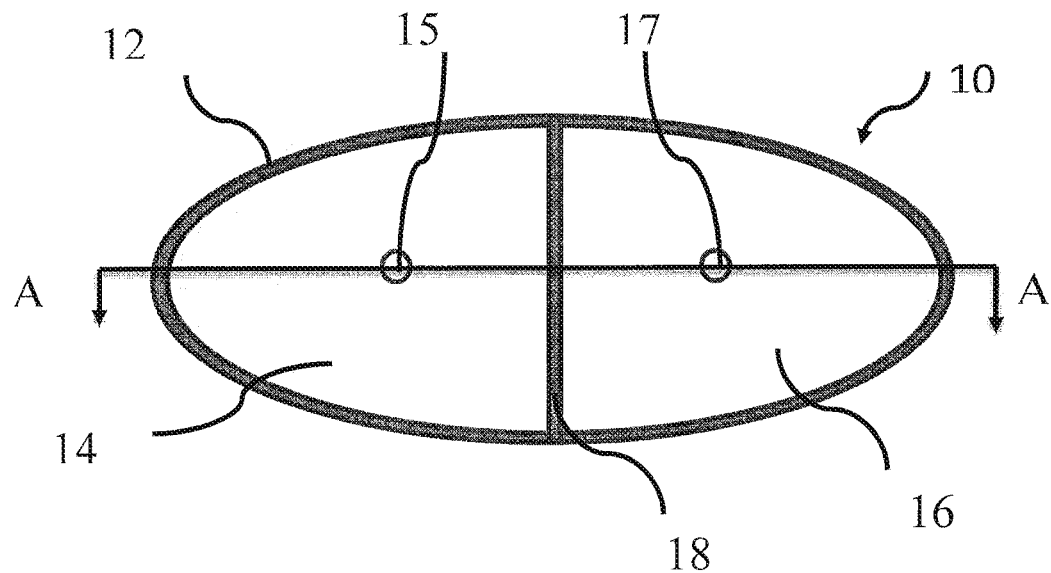
FIG. 2 is a diagram of a top view of a die for making a multi-fill softgel capsule.
Figure 6:
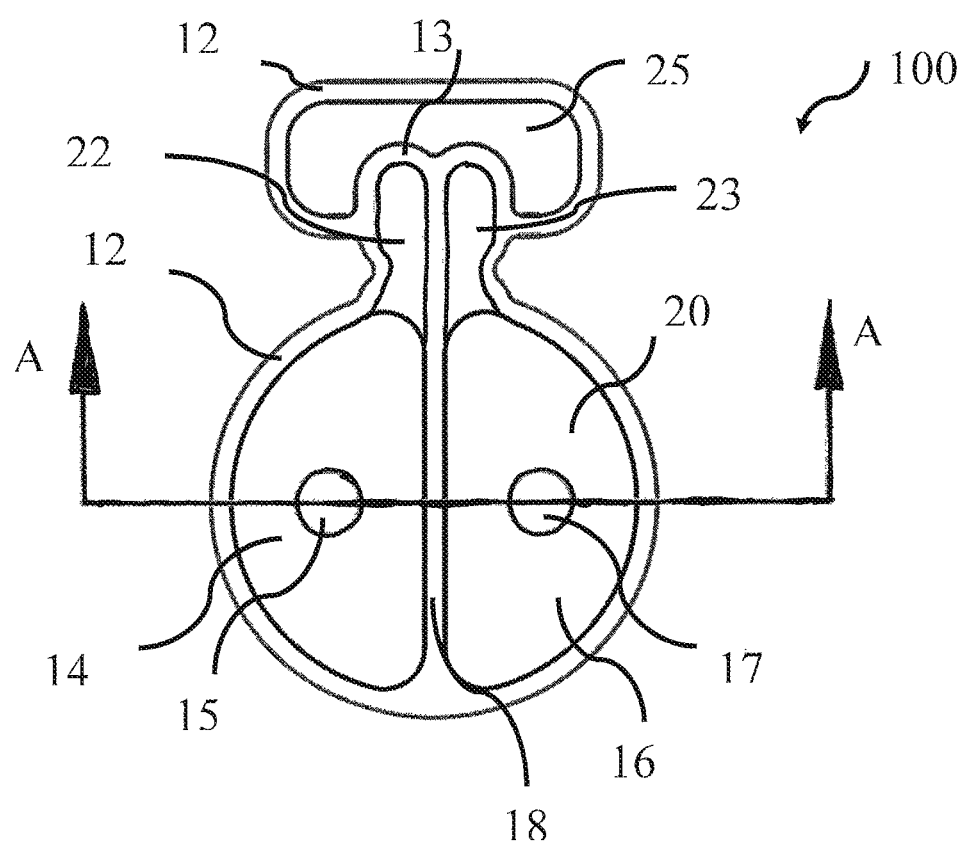
FIG. 6 is a diagram of a top view of a die for making a multi-fill softgel capsule having a twist-off cap. The location of cross-section A-A is indicated.
Figure 7:
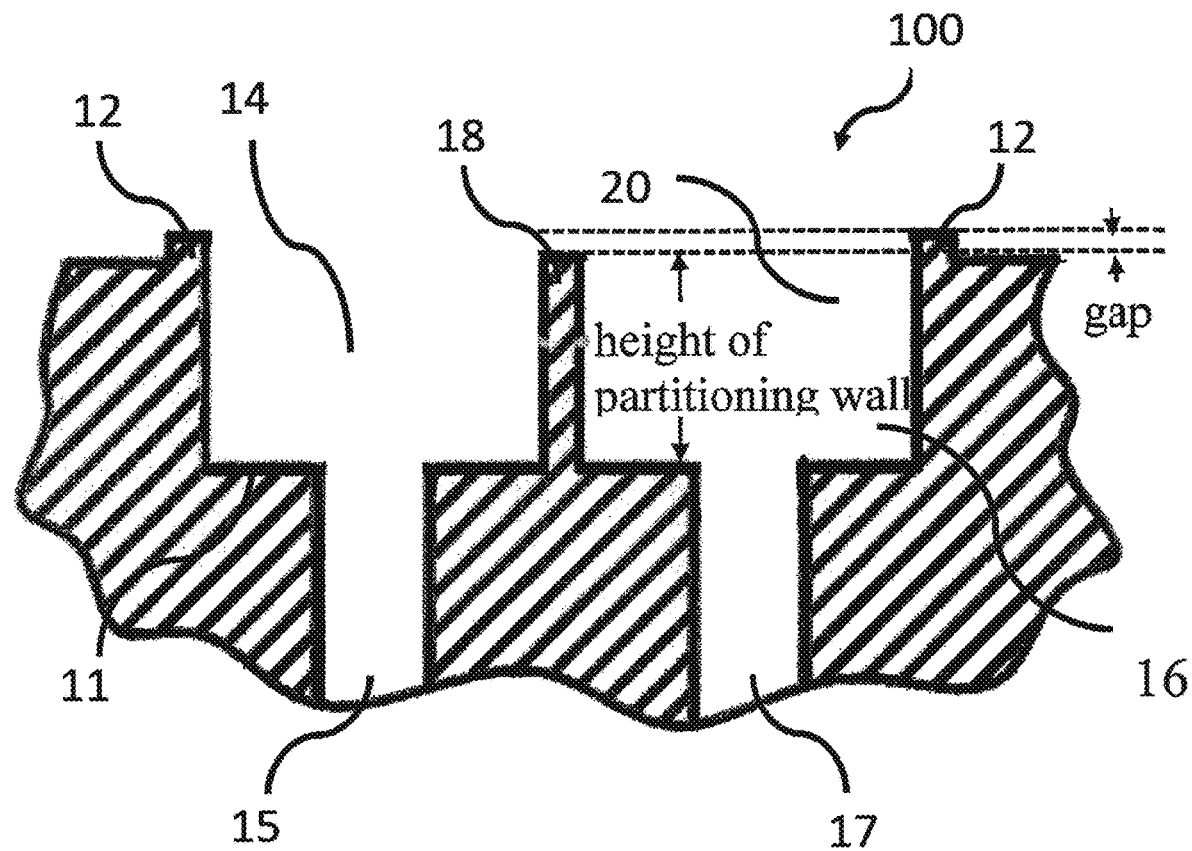
FIG. 7 is a cross-section side view of the die of FIG. 6 at cross-section A-A of the die, as shown in FIG. 6.
Figure 8:
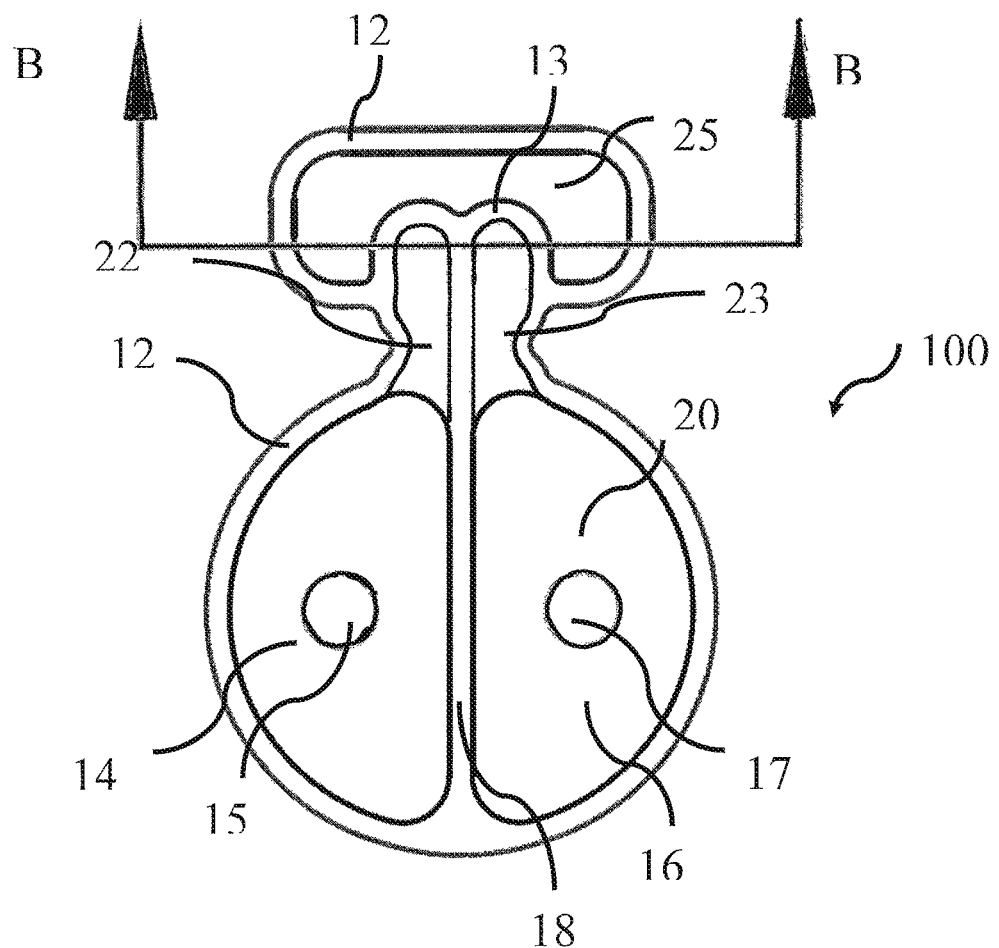
FIG. 8 is a top view diagram of the same die in FIG. 6, showing the location of cross-section B-B near the twist-off cap.
Figure 16:
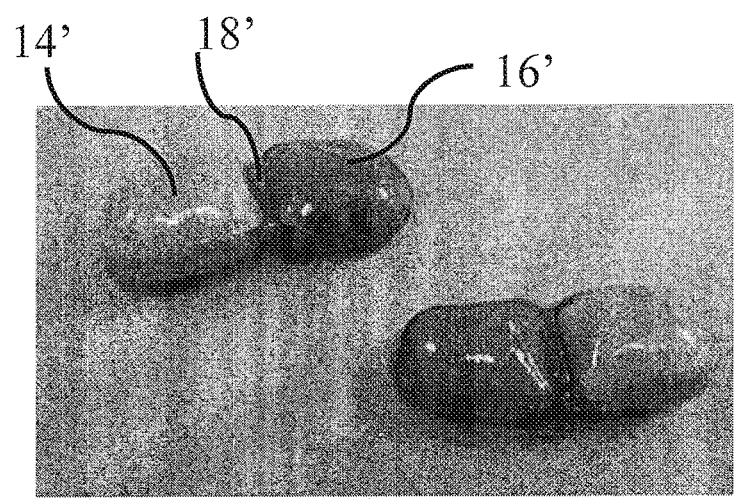
FIG. 16 is a photo of multi-fill softgel capsules produced by the die of FIGS. 5 and 14.
Figure 17:
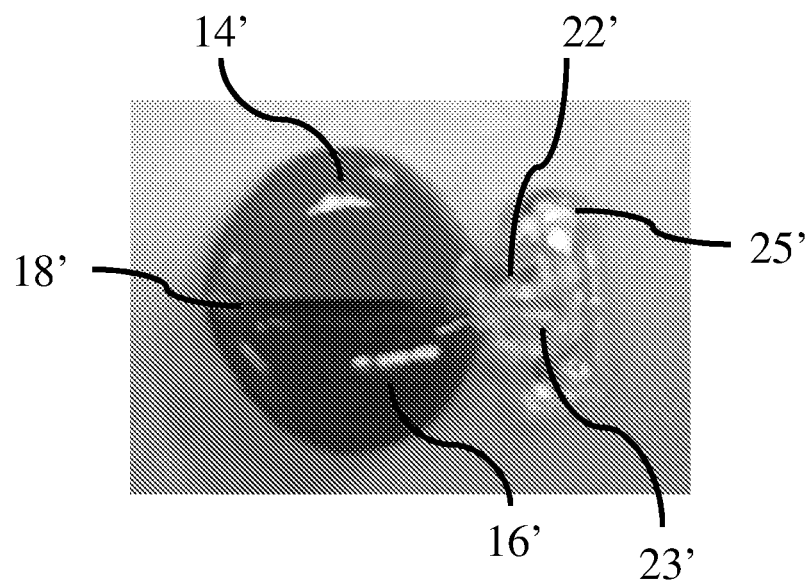
FIG. 17 is a photo of a multi-fill softgel capsule produced by the die of FIGS. 6-8 and 10.

The present disclosure provides a die 10, 100, 200 for producing multi-chamber softgel capsules. The die 10, 100, 200 has its die pocket 20 defined by a die pocket wall 12 and a bottom surface 11. The die pocket 20 is divided into a plurality of chambers 14, 16 by one or more partitioning walls 18, as shown in FIGS. 2, 6, and 8. The die pocket wall 12 and the one or more partitioning walls 18 have their respective top sections defined as lands 29, 39 (FIGS. 20A-20B and 21A-21B). The top of the land 29 along the perimeter of the die pocket wall 12 is in a same plane. The top of the land(s) 39 of the one or more partitioning walls 18 have a lowest point that is lower than the plane by a gap as shown from a side view in FIGS. 3, 4, 7 and 9. One difference between the die 10, 100, 200 of this disclosure and the die 5, 5' of FIG. 1 is that the die 10, 100, 200 of this disclosure has multiple chambers 14, 16 in its die pocket 20, which enables the die 10, 100, 200 to produce a multi-chamber softgel capsule with the multiple chambers 14', 16' separated by one or more barrier seals 18' (FIGS. 16-17).

The land 29 of the die pocket wall 12 is shown in FIGS. 20A-20B. In one embodiment, the top surface of the land 29 is smooth (FIG. 20A). In other embodiments, the land 29 has a recess 19 on its top (FIG. 20B). In yet other embodiments, the recess 19 has a crescent shape when viewed from a side view (FIG. 20B). It is understood that the top of the lands 29 may have different shapes such as rounded, flat, curved, plateaued or angled. In one embodiment, the top of the lands 29 may have a recess forming a semicircular curve with a radius.

Figure 21A:
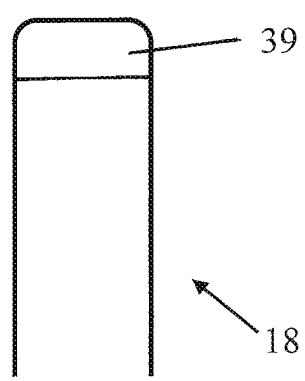
FIGS. 21A-21B are cross-section side views of partitioning walls with a top section thereof called the land. The land can have a smooth top surface (FIG. 21A) or a crescent-shaped recess in its top surface (FIG. 21B).
Figure 21B:
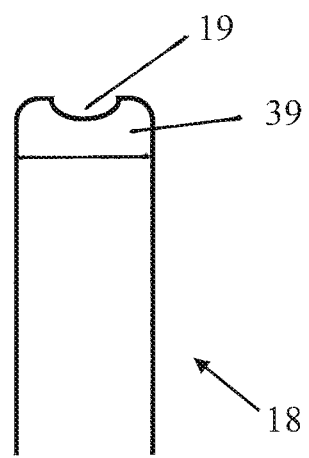

Similarly, the lands of the partitioning wall 18 are shown in FIGS. 21A-21B. In one embodiment, the top surface of the land 39 is smooth (FIG. 21A). In an embodiment, the land 39 has a recess 19 on its top (FIG. 21B). In certain embodiments, the recess 19 has a crescent shape from a side view (FIG. 21B). It is understood that the top of the lands 39 has a shape that is independent of the shape of the land 29, and may be rounded, flat, curved, plateaued or angled. In another embodiment, the top of the lands 39 may have a recess forming a semicircular curve with a radius.

In certain embodiments, the land 29 and the land 39 are not separate pieces adhered to the die pocket wall 12 and the partitioning wall 18, respectively. Rather, the land 29 is a section of the die pocket wall 12 and the land 39 is a section of the partitioning wall 18.

In one embodiment, the top of the land 39 of at least one of the one or more partitioning wall 18 is curved as viewed from chamber 14, 16. In another embodiment, the top of the land 39 of the at least one of the one or more partitioning wall 18 is flat as viewed from the chamber 14, 16. In yet another embodiment, the top of the land 39 of the at least one of the one or more partitioning wall 18 is serrated as viewed from the chamber 14, 16.

As used herein, a "softgel capsule" refers to a soft capsule, such as a gelatin-based capsule, that is provided as a single use form. In some examples, the softgel capsule includes a liquid fill, such as a solution, suspension or semisolid, which is encapsulated by two halves of a capsule shell to form a single, hermetically sealed capsule. In some aspects, the capsule shell can comprise gelatin, a plasticizer, and water. The capsule shell can also include other ingredients such as preservatives, coloring, flavorings, opacifying agents, sweetening agents, acids, salts, medicaments, or other agents to achieve a desired dosage effect. The fill material may be a pharmaceutical formulation, a dietary supplement, a veterinary product, a cosmetic product, or a product for industrial applications (e.g., two part epoxy or polyurethanes). The industrial applications may include two industrial materials that may be used at the point of use to produce a desirable industrial product.

In some aspects, the die 10 of this disclosure is shown in FIG. 2, which has a die pocket 20 divided by a partitioning wall 18 into two chambers 14, 16. The die pocket 20 is defined by a die pocket wall 12 and a bottom surface 11. The top of the land 29 of the die pocket wall 12 is in the same plane. In each chamber 14, 16, there is an air hole 15, 17 at the bottom surface 11 for letting the air out when a gel ribbon covering the die 10 is settling into the chamber 14, 16 to form the recesses for receiving the fill material. The two chambers 14, 16 comprise almost all of the volume of the die pocket 20 in FIG. 2. As shown in the cross-section view of the die 10 in FIG. 3, the top of the land 39 of the partitioning wall 18 is lower than the plane formed by the top of the land 29 of the die pocket wall 12, by a gap.

In operation of some aspects, a gel ribbon is fed and placed on top of a first die 10, with the gel ribbon settling into the chambers 14, 16, for example by suction into the chambers 14, 16 through the air holes 15, 17 or by the pressure of fill material. The settled gel ribbon defines recesses which will become halves of each of the two chambers 14', 16' of a softgel capsule. The gel ribbon also rests on the land 39 of the partitioning wall 18. A mated die 10 also has a gel ribbon settled in and formed the mated recesses. After the two mated dies 10, each with the gel ribbon settled in and formed complementary halves of the chambers 14', 16', are pressed against each other, the gel ribbons are fused under heat along the land 29 of the die pocket wall 12 and the land 39 of the partitioning wall 18 to form a softgel capsule with two chambers 14', 16'. Because the land 39 of the partitioning wall 18 is lower than the land 29 of the die pocket wall 12, the gel fused along the land 39 of the partitioning wall 18 will form a barrier seal 18' to separate the two chambers 14', 16' of the softgel capsule yet still linking the two chambers 14', 16' together. On the other hand, the gel ribbons along the land 29 of the die pocket wall 12 are pressed together tightly such that the formed softgel capsule can be easily severed from the remaining gel ribbons. The two chambers 14', 16' of the softgel capsule may be injected with different fill materials, thus resulting in a softgel capsule with two chambers 14', 16' filled with two different fill materials.

The formed softgel capsules may be cut out from the remaining gel ribbons by punching. Alternatively the softgel capsules can be easily pushed out of the remaining gel ribbons when the mated dies 10 are pressed sufficiently tightly together along the land 29 of the die pocket wall 12 that the gel ribbons surrounding each capsule is sufficiently thin. In one aspect, the two-chamber softgel capsules produced from the die 10 of FIG. 4 are shown in FIG. 16.

Figure 4:
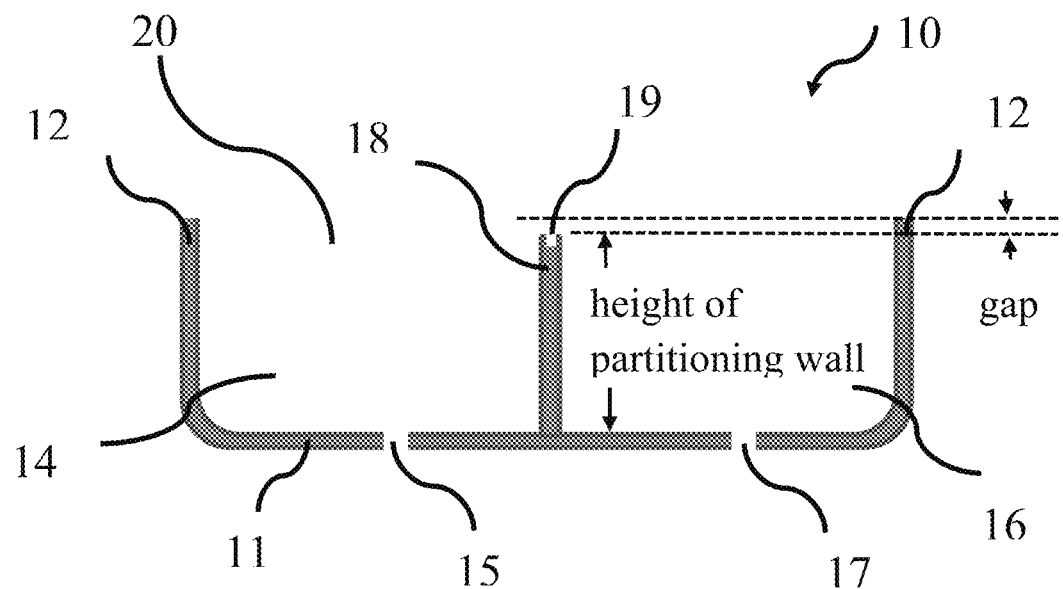
FIG. 4 is another cross-section view of the die of FIG. 2 as viewed from a side view of the die at cross-section A-A of FIG. 2.
Figure 5:
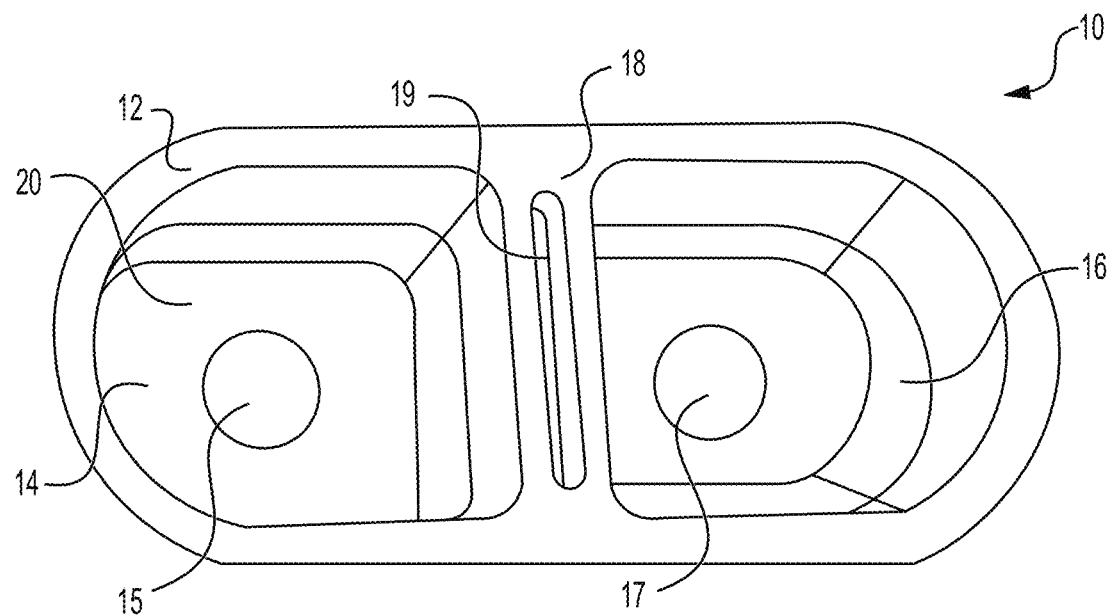
FIG. 5 is a photo of the die of FIG. 4.

In some aspects, the top surface of the land 39 of the partitioning wall 18 may itself have a recess 19 on the top along the length of the land 39 of the partitioning wall 18, as shown in FIGS. 4 and 5. The recess 19 on the top of the land 39 of the partitioning wall 18 will create a thickened area along the barrier seal 18' between the two chambers 14', 16' of the softgel capsule. The thickened area can strengthen the barrier seal 18'. A photo of die 10 of FIG. 4 is shown in FIG. 5.

In some other aspects, the die 100 has an area that forms a twist-off cap 25 (FIG. 6) as shown from above the die. The two chambers 14, 16 of this die 100 each in fluid connection with a discharge channel 22, 23 respectively. The two chambers 14, 16 comprise a majority of the volume of the die pocket 20. The discharge channels 22, 23 and twist-off cap 25 area comprise a small portion of the volume of the die pocket 20. The partitioning wall 18 extended from between the chambers 14, 16 to between the discharge channels 22, 23. The discharge channels 22, 23 are separated from the twist-off cap 25 by a channel wall 13, which connects to the die pocket wall 12 and partitioning wall 18. A cross-section view of the die 100 of FIG. 6 at the location A-A is shown in FIG. 7. The chambers 14, 16 are half-circular in shape with air holes 15, 17 at or near the center of the respective chambers 14, 16. The lowest point of the top of the land 39 of the partitioning wall 18 is lower than the plane with the top of the land 29 of the die pocket wall 12 by a gap (FIG. 7).

Figure 9:
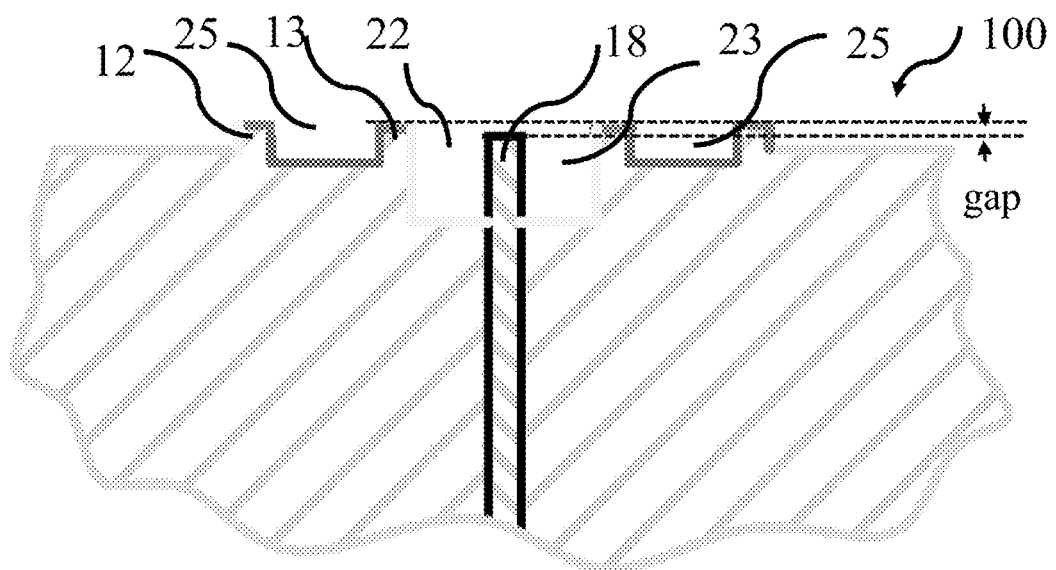
FIG. 9 is a cross-section side view of the die of FIG. 8 at cross-section B-B of the die as shown in FIG. 8.

FIG. 9 is a cross-section view at B-B of the die 10 as indicated in FIG. 8, providing a better view of the twist-off cap 25 and it vicinity area with the two discharge channels 22, 23. The partitioning wall 18 extends to the twist-off cap 25 and separates a small and shallow fill area into two discharge channels 22, 23. The discharge channel 22, 23 are in fluid connection with the respective chambers 14, 16. The channel wall 13 and the die pocket wall 12 define a shallow space to form the twist-off cap 25. The twist-off cap 25 area will be filled with the gel to form the twist-off cap 25' of the softgel capsule, which does not contain any fill material.

In one aspect, both of the land 39 of the partitioning wall 18 and channel wall 13 are lower than the land 29 of the die pocket wall 12 (FIG. 9). Particularly, the land 39 of the partitioning wall 18 has a larger gap than the channel wall 13, both in comparison with the plane having the top of the land 29 of the die pocket wall 12 (FIG. 9). The die 100 of this aspect produces a softgel capsule (FIG. 17) having the discharge channels 22', 23' fluidly connected to the chambers 14', 16'. In other words, the discharge channels 22', 23' may be filled with the same fill material as its respectively connected chambers 14', 16'. The barrier seal 18' (separating the chambers 14', 16' and discharge channels 22', 23') is thicker than the channel seal that separates the channels 22', 23' from the twist-off cap 25'. This is because the land 39 of the partitioning wall 18 has a larger gap than the channel wall 13, to the plane having the top of the land 29 of the die pocket wall 12. After the twist-off cap 25' of such a softgel capsule is twisted off, the channel seal connected to the twist-off cap 25' is ruptured, which exposes the discharge channels 22', 23'. The fill materials may be then released/sprayed from the chambers 14' and 16' through the discharge channels 22', 23'.

Figure 10:
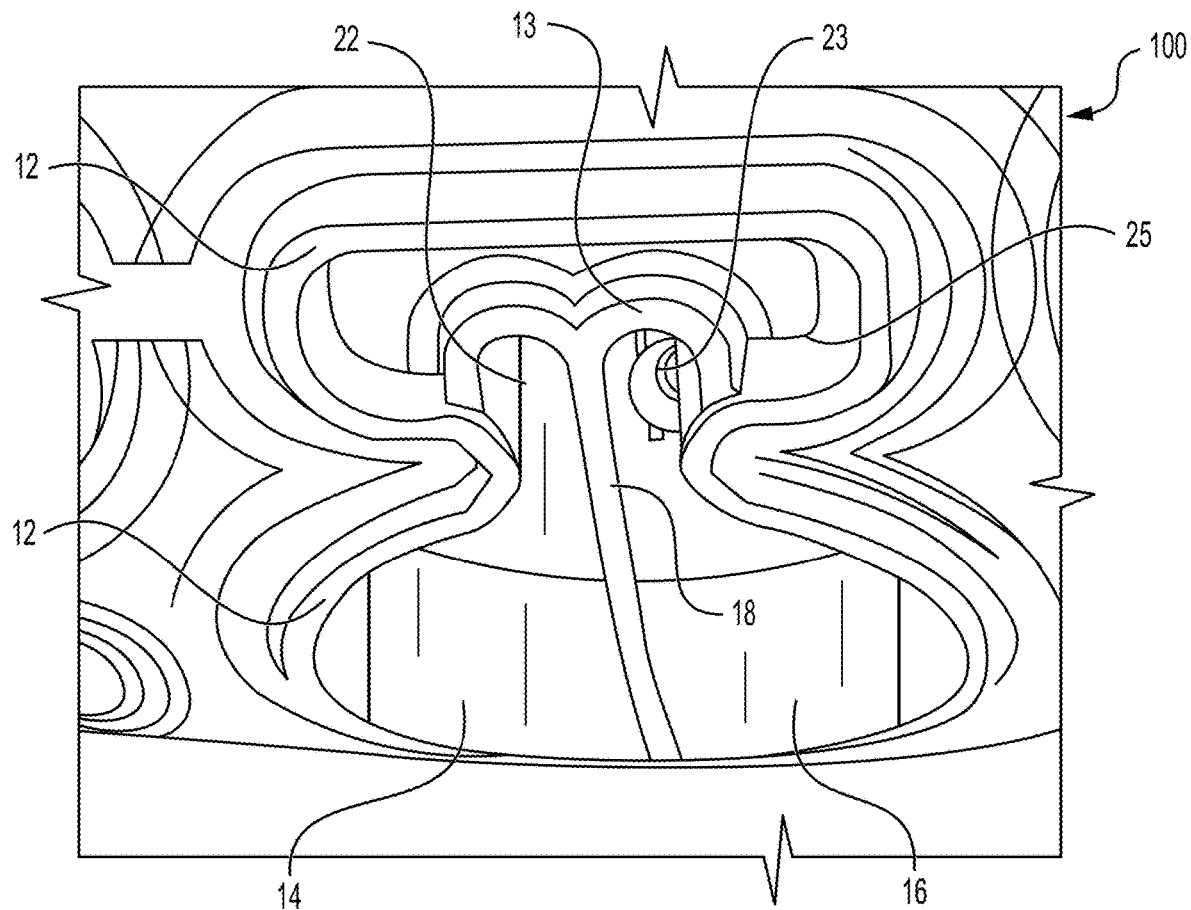
FIG. 10 is a photo of the die of FIGS. 6 and 8.
Figure 11:
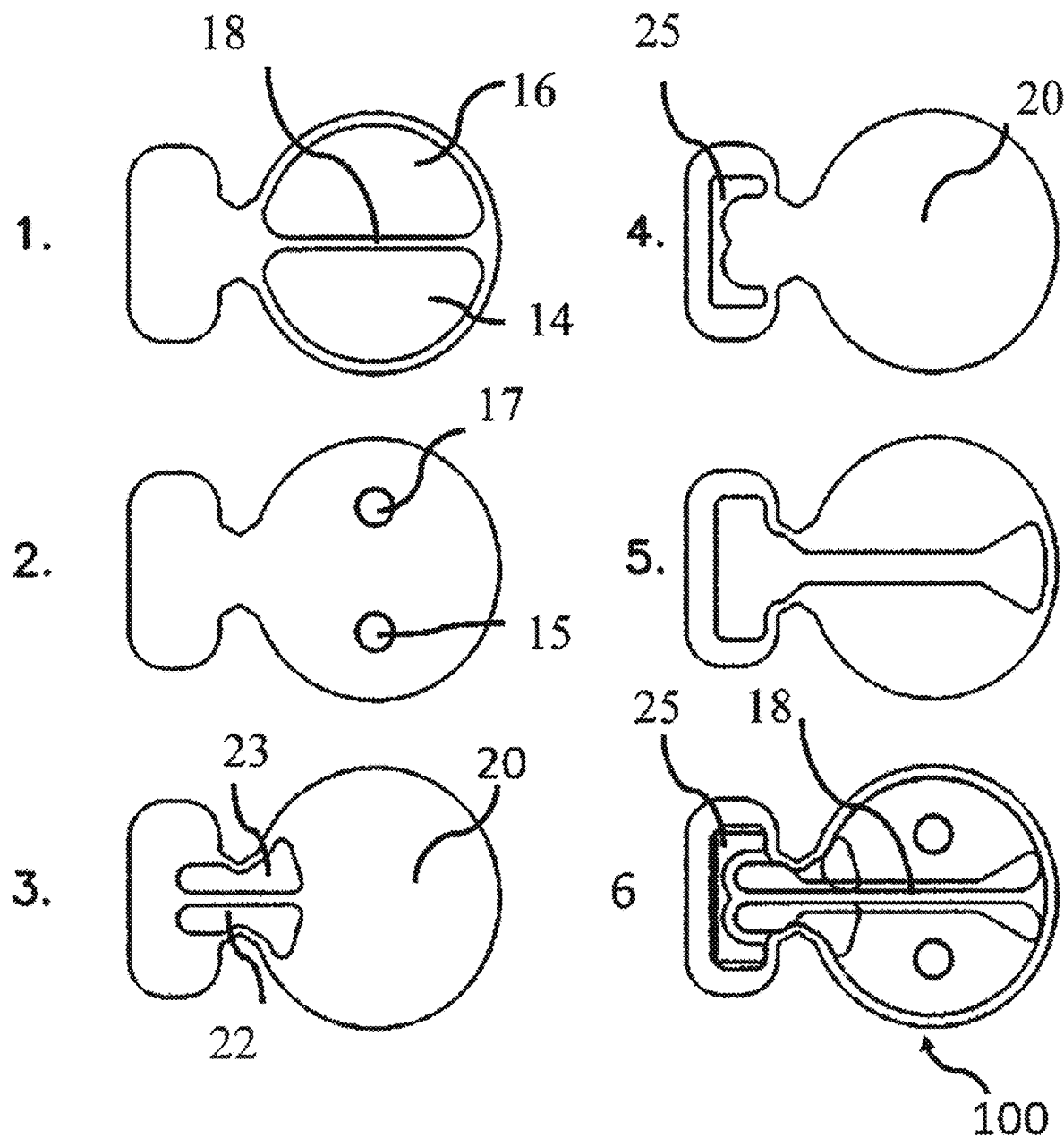
FIG. 11 is a series of diagrams showing different features of the die of FIG. 6 in separate diagrams.

A photo of die 100 of FIGS. 6 and 8 is shown in FIG. 10. The channel wall 13 connects to the partitioning wall 18 at the middle and to the die pocket wall 12 at both sides near the neck area of the twist-off cap 25. The discharge channels 22, 23 are each in fluid connection with the chambers 14, 16 respectively. FIG. 11 shows the top view of individual features of the die 100 of FIG. 6 in separate diagrams 1-5, with all the individual features merged into the diagram 6. Particularly, diagram 1 of FIG. 11 shows the two chambers 14, 16 and the partitioning wall 18 that separates them. Diagram 2 of FIG. 11 shows the two air holes 15, 17 in the two chambers 14, 16. Diagram 3 of FIG. 11 shows the two discharge channels 22, 23, separated by the partitioning wall 18, and the die pocket 20. Diagram 4 of FIG. 11 shows the twist-off cap 25 and the die pocket 20. Diagram 5 of FIG. 11 shows a shoulder area around the partitioning wall 18 and the discharge channels 22, 23. Diagram 6 of FIG. 11 shows all the features from diagrams 1-5 together in the same diagram.

Figure 18:
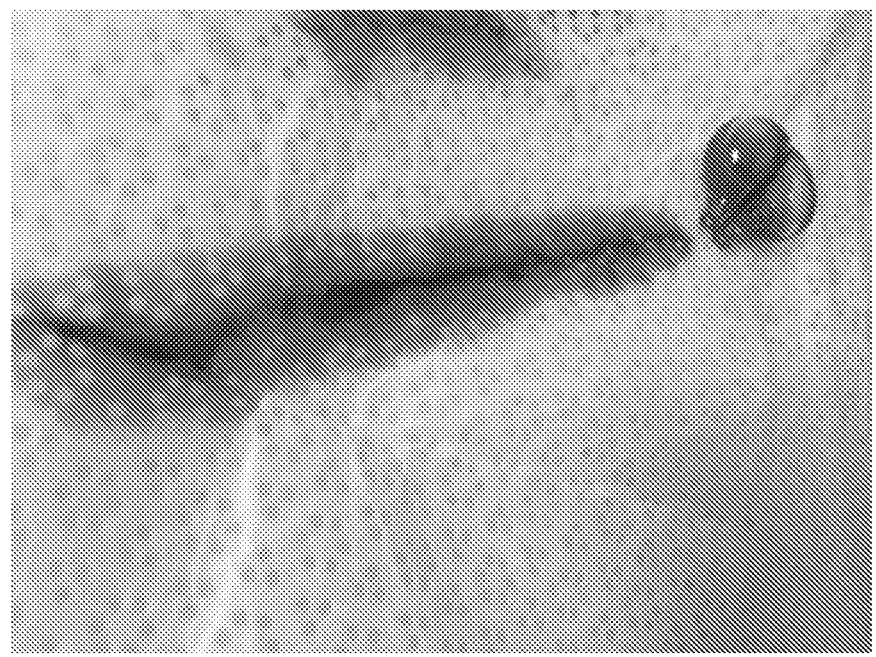
FIG. 18 is a photo of the multi-fill softgel capsule of FIG. 17 and the two liquid fill materials sprayed on a piece of paper.

The die 100 of FIG. 6 can produce a two-chamber softgel capsule with a twist-off cap 25' and each of its chambers 14', 16' may contain a different fill material (FIG. 17). Before being used, the twist-off cap 25' of the softgel capsule may be twisted and separated from the main body of the softgel capsule (FIG. 18). The separation of the twist-off cap 25' exposes the discharge channels 22', 23', which allows the fill materials in both of the chambers 14', 16' to be released. The softgel capsule may be compressed to spray the two fill materials in each of the chambers 14', 16' through the discharge channels 22', 23' (FIG. 18).

Figure 12:
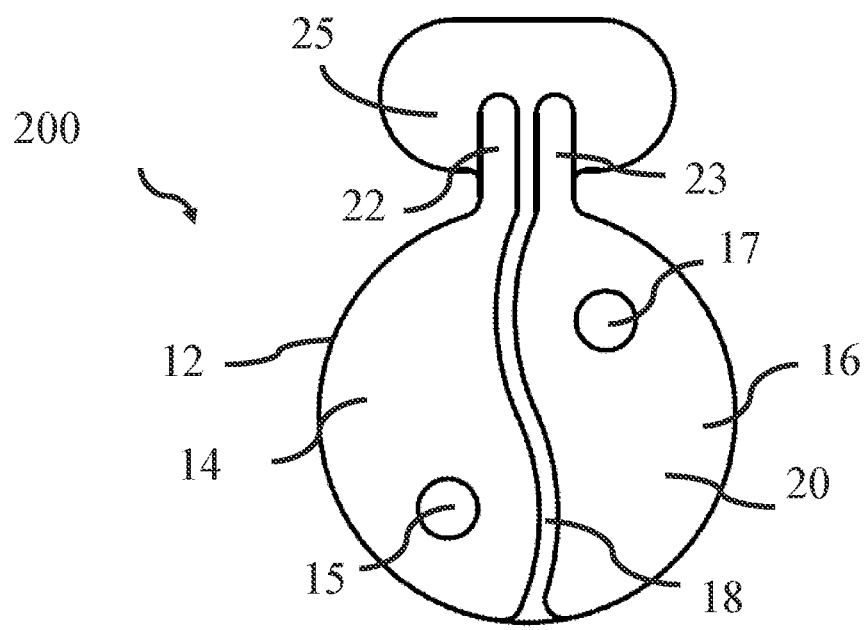
FIG. 12 is a diagram of a die for making a multi-fill softgel capsule having a twist-off tab.

In another aspect, a variation of the die 100 of FIG. 6 is shown in FIG. 12 with a die 200. The partitioning wall 18 in this aspect is not a straight line, but instead a curved line that also separates the two chambers 14, 16. Further, the air holes 15, 17 may be located at locations away from the center of the respective chambers 14, 16.

Figure 13:
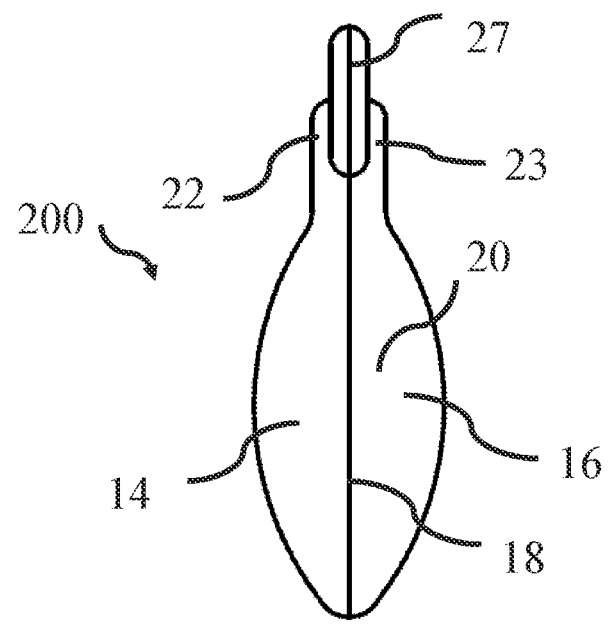
FIG. 13 is a top view of a die for making a multi-fill softgel capsule as shown from a side view.

FIG. 13 shows another variation of the die 100 of FIG. 6 with a die 200. The die 200 of this variation has a twist-off tab 27 is in the shape of a bar, which at least partially separate the two discharge channels 22, 23. The discharge channels 22, 23 are in fluid connection, respectively with the two chambers 14, 16.

In some aspects, the bottom surface 11 of the die pocket 20 may be flat. In another aspect, the flat bottom surface 11 has rounded junctions with the die pocket wall 12, instead of angled junctions. In yet another aspect, the bottom surface 11 is curved (instead of flat) with its deeper portion near the center of the die pocket 20. In yet another aspect, the bottom surface 11 is a continuous curve near or up to the top of the die pocket wall 12 thus forming a die pocket 20 that is a half or a portion of a sphere, a half or a portion of an oval, or a portion of a heart.

In some aspects, the die pocket 20 may have the overall shape of a portion of a shape selected from a non-limiting examples of sphere, oval, cube or rounded cube, cuboid or rounded cuboid, heart, water drop, animals such as fish or bear, triangle, or pear.

In some aspects, the die pocket 20 has a bottom surface 11 that is a single point or a line (straight or curved), with the die pocket wall 12 extending into the die pocket 20 and joining at the point or line. For example, the die pocket 20 may have a cone shape or a pyramid shape with the tip point at the bottom of the die pocket 20 as the bottom surface 11. The pyramid shape may be three-sided, four-sided, five-sided, six-sided, eight-sided, or ten-sided pyramid. For another aspect, the die pocket 20 may have the shape of a ridge with the tip being a line at the bottom of the die pocket 20, and where the line is the bottom surface 11.

Figure 3:
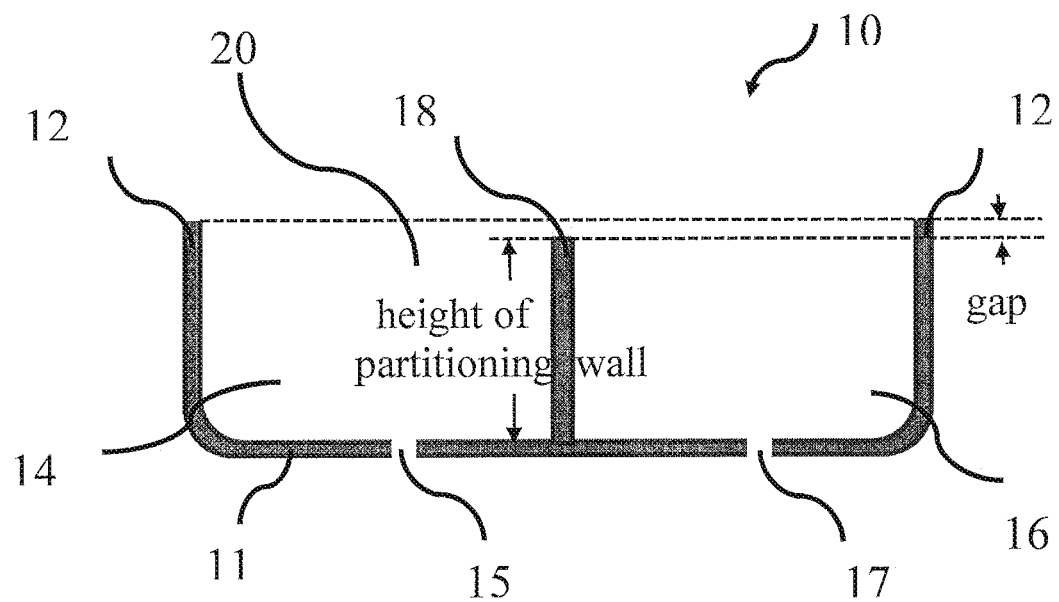
FIG. 3 is a cross-section view of the die of FIG. 2 as viewed from a side view of the die at cross-section A-A of FIG. 2.

The die 10, 100, 200 of this disclosure has a lowest point of the top of the land 39 of the partitioning wall 18 lower than the plane of the top of the land 29 of the perimeter of the die pocket wall 12 by a gap. The top of the land 29 of the die pocket wall 12 is in a plane, which allows for the production of the barrier seal 18' of the softgel capsule between the two chambers 14', 16' (FIGS. 3-4 and 7). In some aspects, a size of the gap is less than the thickness of the gel ribbon used to make the softgel capsules such that the gel ribbons are pressed tightly together by the lands 39 of the partitioning walls 18 of mated dies 10 and fused under heat to make the barrier seal 18'. In one aspect, the gap is less than about 95%, or less than about 90%, or less than about 85%, or less than about 80%, or less than about 75%, or less than about 70%, or less than about 65%, or less than about 60%, or less than about 55%, or less than about 50%, or less than about 45%, or less than about 40%, or less than about 30%, or less than about 20%, of the thickness of the gel ribbons. Therefore, in this aspect, the gap may be adjusted according to the thickness of the gel ribbons for producing the softgel capsules.

In one aspect, a size of the gap is in the range of from about 0.0508 mm (0.002 inch) to about 2.54 mm (0.1 inch), or from about 0.508 mm (0.02 inch) to about 2.032 mm (0.08 inch), or from about 0.508 mm (0.02 inch) to about 1.524 mm (0.06 inch), or from about 0.762 mm (0.03 inch) to about 1.27 mm (0.05 inch), or about 1.016 mm (0.04 inch).

In some aspects, the partitioning wall 18 is perpendicular to the plane across the top of the die pocket wall 12. The thickness of the partitioning wall 18 may be in the range of from about 0.254 mm (0.01 inch) to about 2.54 mm (0.1 inch), or from about 0.508 mm (0.02 inch) to about 2.032 mm (0.08 inch), or from about 0.508 mm (0.02 inch) to about 1.524 mm (0.06 inch), or from about 0.762 mm (0.03 inch) to about 1.27 mm (0.05 inch), or about 1.016 mm (0.04 inch). In some other aspects, the thickness of the partitioning wall 18 can be larger than 2.54 mm (0.1 inch), or larger than 5.08 mm (0.2 inch), or larger than 7.62 mm (0.3 inch).

In some aspects, the partitioning wall 18 has a different thickness at different portion of the partitioning wall 18. In one example, the partitioning wall 18 may have a larger thickness at the portion near the bottom surface 11, but a smaller thickness at the portion near the top of partitioning wall 18. In another aspect, the partitioning wall 18 has a thickness that decreases, preferably continuously, from proximate to the bottom surface 11 to the land the partitioning wall 18 such that it is easier to disengage the partitioning wall 18 from the produced softgel capsule.

In some other aspects, the die 10, 100, 200 of this disclosure has two or more chambers 14, 16. In one aspect, the die 10 may have two or more parallel partitioning walls 18, thus dividing the die pocket 20 into three or more chambers 14, 16 as viewed in a top view above the die. In another aspect, the die 10, 100, 200 has multiple partitioning walls 18 intersecting at the same point and form a star shape, for example the center of the star being at the center of the die pocket 20. The star may have three arms, or four arms, or five arms, or six or more arms, thus dividing the die pocket 20 into three, or four, or five, or six or more chambers 14, 16. In yet another aspect, the die 10, 100, 200 has partitioning walls 18 that are a grid shape, which can divide the die pocket 20 into multiple chambers 14, 16. In yet another aspect, the die 10, 100, 200 has partitioning walls 18 that are intersecting curves, which can also divide the die pocket 20 into multiple chambers 14, 16. A person skilled in the art would appreciate that different configurations of the die pocket 20 will require suitable modifications to the injection pump.

In yet some other aspects, the chambers 14, 16 of the die 10, 100, 200 of this disclosure have different sizes which can encapsulate different amounts of fill materials in one or more of the chambers 14, 16. For example, one chamber 14 can be larger than the other chamber 16, thus producing softgel capsules with a large chamber 14' and a small chamber 16'. The large chamber 14' can contain a larger amount of one fill material than the other fill material in the small chamber 16'. Therefore, a single softgel capsule produced by the die 10, 100, 200 of this disclosure can contain two pharmaceutical formulations at different amounts by changing the volumes of their respective chambers, or two cosmetic products can be included at different amounts by changing the volumes of their respective chambers. In some other aspects, the amount of ingredients in each of the chambers may vary by using different concentrations in the respective fill materials so that the volume of their respective chambers does not need to vary.

In one aspect, the die 10 of FIG. 4 has a depth of from about 2 to about 18 mm, or from about 3 to about 15 mm, or from about 4 to about 12 mm, or from about 5 to about 10 mm, or from about 6 to about 8 mm.

In another aspect, the recess 19 of die 10 of FIG. 4 has a thickness of from about 0.4 to about 4 mm, or from about 0.6 to about 3 mm, or from about 0.8 to about 2 mm, or from about 0.8 to about 1.5 mm.

In one aspect, the die 10 of FIG. 4 has chambers 14, 16 of 6.604 mm (0.260 inch) deep. The gap between the lowest point of top of the land 39 of the partitioning wall 18 and the plane having the top of the land 29 of the die pocket wall 12 is 1.016 mm (0.040 inch). The recess 19 on the top of the partitioning wall 18 has a thickness of 1.016 mm (0.04 inch).

In another aspect, the die 100 of FIG. 6 has chambers 14, 16 of 0.25 inch deep. The gap between the lowest point of the top of the land 39 of the partitioning wall 18 and the plane formed by the top of the land 29 of the perimeter of the die pocket wall 12 is 1.016 mm (0.040 inch). The thickness of the partitioning wall 18 is 1.016 mm (0.04 inch). The discharge channels 22, 23 have a depth of 3.048 mm (0.12 inch). The air holes 15, 17 are circular with a diameter of 3.302 mm (0.13 inch).

In yet another aspect, the air holes 15, 17 have a diameter in the range of from about 1 to about 5 mm, or from about 1.5 to about 4 mm, or from about 2 to about 4 mm, or from about 3 to about 4 mm.

In yet other aspects, the die 10, 100, 200 of this disclosure may have a variety of shapes to make softgel capsules of different shapes (FIG. 19). In diagram 1 of FIG. 19, the softgel capsule has an overall oval shape and its two chambers 14', 16' are separated by a barrier seal 18' across the capsule near the middle of the softgel capsule. In diagram 2 of FIG. 19, the softgel capsule has two circular or oval shaped chambers 14', 16' linked by a barrier seal 18'.

In some aspects, to make the die 100 of FIG. 6 with two chambers 14, 16 and a twist-off cap 25, a five step process may be used.
  1. Design the chambers 14, 16 (this area holds most of the fill materials).
  2. Place the air hole 15, 17 at each chamber 14, 16 (allowing air flow into or out of the chambers 14, 16).
  3. Create the twist-off cap area 25 (this area is separated from the chambers 14, 16 and steps down in depth. This area has a specially designed recess that makes twisting the cap 25' easy and creates an accurate hole diameter to release the fill materials of the softgel capsule).
  4. Design the channel wall 13 (this creates a wall to keep the fill material from leaking to the twist-off area 25).
  5. Create the shoulder area (this area is around the partitioning wall 18 and discharge channel 22, 23 area, which may be 0.05 inch deep, causing the gel to seal down properly).

In some aspects, this disclosure provides a pair of mated dies 10, 100, 200 suitable for producing a multi-chamber softgel capsule, each of the pair of the dies 10, 100, 200 comprises a die pocket 20 defined by a die pocket wall 12 and a bottom surface 11, and one or more partitioning walls 18 dividing the die pocket 20 into two or more chambers 14, 16. The die pocket wall 12 and the one or more partitioning walls 18 have their respective top sections defined as lands 29, 39. The partitioning walls 18 of the pair of mated dies 10, 100, 200 have heights such that when the pair of dies 10, 100, 200 are mated, there is a gap between the top of the land 39 of each of the partitioning walls 18 of the pair of mated dies 10, 100, 200.

In one aspect, a size of the gap between the top of the land 39 of the partitioning walls 18 of the pair of mated dies 10, 100, 200 is in a range from about 0.508 mm (0.02 inch) to about 5.08 mm (0.2 inch), or from about 1.016 mm (0.04 inch) to about 4.064 mm (0.16 inch), or from about 1.016 mm (0.04 inch) to about 3.048 mm (0.12 inch), or from about 1.524 mm (0.06 inch) to about 2.54 mm (0.1 inch).

In another aspect, the gap between the top of the land 39 of the partitioning walls 18 of the pair of mated dies (10) is less than about 95%, or less than about 90%, or less than about 85%, or less than about 80%, or less than about 75%, or less than about 70%, or less than about 65%, or less than about 50%, or less than about 45%, or less than about 40%, or less than about 30%, or less than about 20%, of the total thickness of a gel ribbon located between the pair of mated dies (10).

The die 10, 100, 200 of this disclosure is suitable for producing softgel capsules that encapsulate two or more fill materials in separate chambers 14', 16'. The two or more fill materials are not mixed in the softgel capsule, thus preventing any incompatibility issues between the fill materials. For example, the softgel capsule may be filled with two cosmetic products in two separate chambers 14', 16' for a single use. A customer may twist off the twist-off cap 25' and applies the encapsulated cosmetic products, which may then be mixed after released from the softgel capsule.

Figure 14:
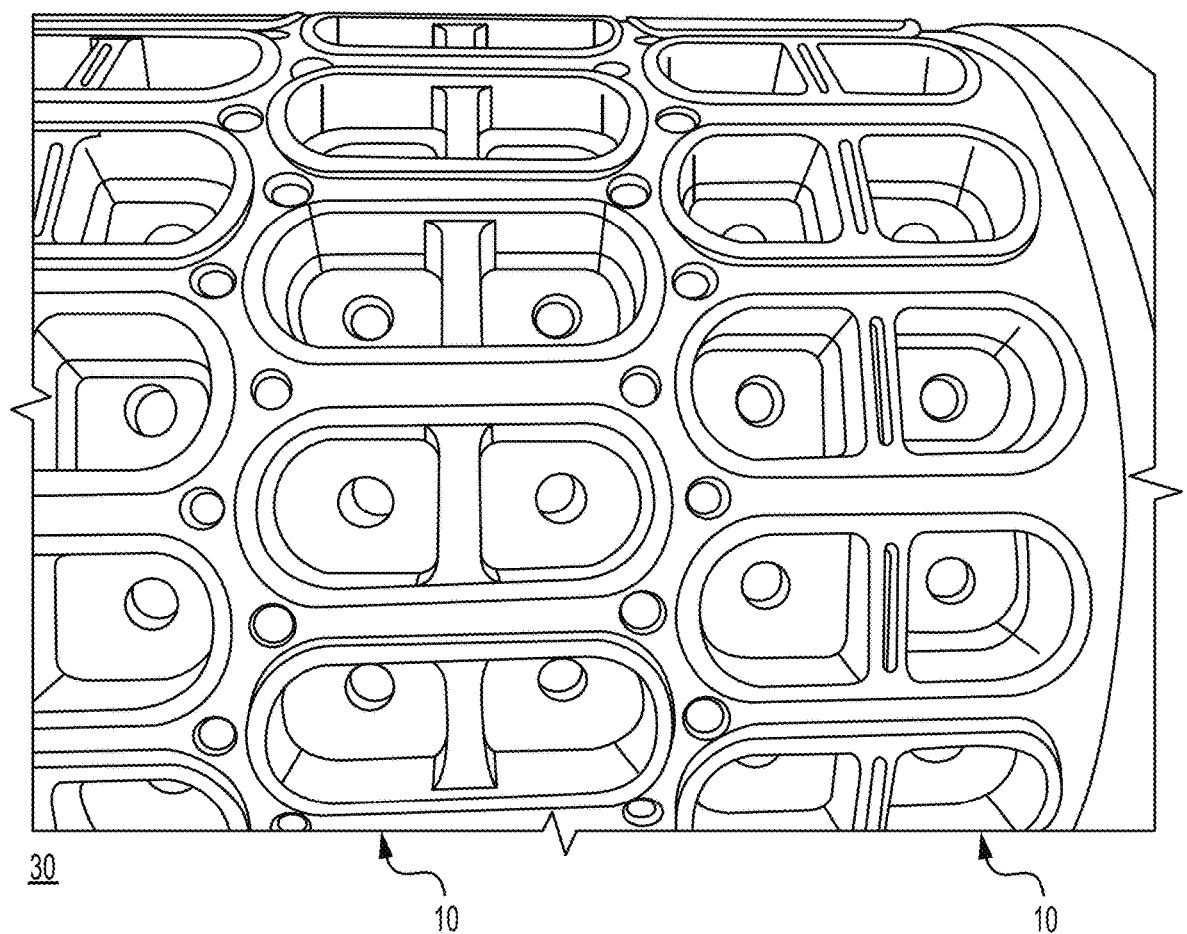
FIG. 14 is a photo of the dies of FIG. 1 on a die roll for use in a rotary die encapsulation machine.
Figure 15:
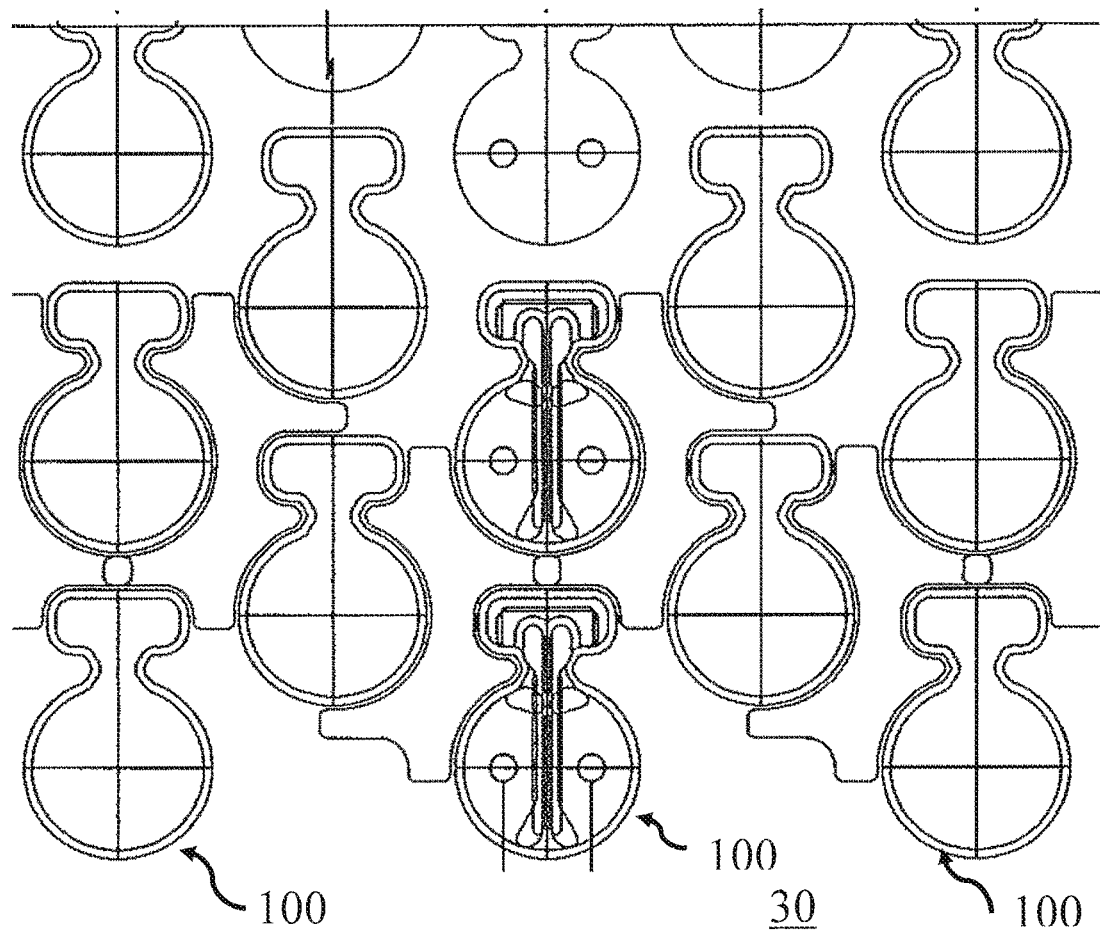
FIG. 15 is a diagram of the die of FIGS. 6 and 8 on a die roll for use in a rotary die encapsulation machine.

In some aspects, a plurality of the dies 10, 100, 200 of this disclosure are placed on a die roll 30 that are suitable to be used in a rotary die encapsulation machine (FIGS. 14-15). In one example, a plurality of the dies 10 of FIG. 2 are on the die roll 30 (FIG. 14). In another example, a plurality of the dies 100 of FIG. 6 are on the die roll 30 (FIG. 15).

As used herein, a "die roll" refers to a roll with dies 10, 100, 200 on the surface of the roll that are suitable for making and filling softgel capsules in a rotary die encapsulation machine which mates the dies of one die roll with dies of another die roll. Each die roll 30 of the mated pair contains on its surface a series of mated dies 10, 100, 200 for the formation of a softgel capsules. The series of dies 10, 100, 200 on the surface of each die roll 30 are arranged, for example, in rows extending along the axial length of the die roll 30, with the series of rows also extending around the die roll 30. In certain examples, the rows can be configured in a pattern, such as an offset pattern, to maximize the number of dies 10, 100, 200 on the surface of a die roll 30.

The die roll 30 may be substantially cylindrical, and rotate about a fixed axis of the die roll 30. Alternatively the die roll 30 may have a substantially polygonal cross-section, for example octagonal. The axes of two mated die rolls 30 can be sprung loaded towards each other. The die rolls 30 may be arranged to form one softgel capsule at a time, using the plurality of dies 10, 100, 200 in succession as the die rolls 30 rotate. Alternatively the dies 10, 100, 200 may be arranged to form a plurality of softgel capsules at once, side-by-side across the width of the gel ribbons. In certain embodiments, a heater is associated with the die rolls 30 to provide heating of the gel ribbons to soften them such that they are deformed for settling into the chambers 14, 16 and the contacting gels are fused for forming the softgel capsules.

The die roll 30 can be any suitable width from end to end—as well as any suitable diameter—that is adaptable and configurable for use in conventional rotary die encapsulation machines known in the art. In certain examples, the width of the die roll 30 can be about 25 cm, such as from about 23 to about 27 cm, or from about 24 to about 26 cm, or from 25 to about 26 cm long. In some other examples, the diameter of the die roll 30 can be about 15 cm, such as from about 13 to about 17 cm, or from about 14 to about 16 cm, or from about 15 to about 16 cm.

In some aspects, the die roll 30 can include from about 5 to about 30 rows of dies 10, 100, 200, with each row including from 25 to 50 dies 10, 100, 200. In one example, the die roll 30 can include from about 7 to about 22 rows of dies 10, 100, 200, with each row including from 30 to 46 dies 10, 100, 200. In one aspect, the shape of the dies 10, 100, 200 can determine the most efficient arrangement of the dies 10, 100, 200 on the surface of the die roll 30. In an example, the dies 10, 100, 200 are arranged on the surface so as to maximize the number of dies 10, 100, 200 on the die roll 30. This enables producing a maximum number of softgel capsules by the die roll 30 for each rotation.

A pair of mated die rolls 30 with mated rows of dies 10, 100, 200 on the surfaces of the respective die rolls 30 can be used and/or adapted for use in conjunction with a variety of softgel encapsulation machines. In an example, the die rolls 30 can be adapted for use in conventional rotary die encapsulation machine similar to those known in the art. The two mated die rolls 30 rotate in opposite directions as part of the encapsulation machine. As gel ribbons pass through the mated die roll 30, the mated die rolls 30 cut and fill the chambers 14', 16' of the softgel capsule with the fill materials. The rotary die encapsulation machine can include any other components for use in the manufacture a softgel capsule, such as a heating wedge, nip, injection pump, gelatin film presses, feeders, guide rollers, and the likes.

In some aspects, the die 10, 100, 200 or die roll 30 of this disclosure can be constructed with one or more high strength materials. Some examples of suitable materials include aluminum, brass, hardened steel, stainless steel, bronze, iron, die cast zinc, etc. Stainless steel includes those steels containing sufficient chromium to render the same corrosive-resistant, commonly at least about 10% chromium by weight. For example, the stainless steel employed may be selected from the series including Types 309, 414, 440 and 446.

The die 10, 100, 200 or die roll 30 of this disclosure may also be constructed using a high wear-resistance and hot strength alloy, such as alloys based on Co, Ni, or Mo. Examples include zinc, magnesium, aluminum, brass or bronze alloys, which have excellent physical properties of hardness and high tensile strength.

In some other aspects, the die 10, 100, 200 of this disclosure, especially when a plurality of the dies 10, 100, 200 are on a die roll 30, are suitable to be used with the multiple-fluid injection pump and filling wedge of U.S. patent application Ser. No. 15/049,961, filed on Feb. 22, 2016, which is hereby incorporated by reference herein. The multiple-fluid injection pump may be used to inject different fill materials into different chambers 14', 16' of the same softgel capsule produced by the die 10, 100, 200 of this disclosure.

The gel ribbon suitable for use with the die 10, 100, 200 to produce softgel capsules may be made from gelatin, or a water-soluble cellulose derivative, such as hydroxypropyl methyl cellulose or hydroxypropyl cellulose, which are approved for use with pharmaceuticals and food. Other suitable gel materials for the gel ribbons include edible seaweed-derived polymers such as sodium alginate (E401), propylene glycol alginate (E405) or agar-agar (E406). Some suitable cellulose derivatives are hydroxypropyl cellulose (E463), and methyl ethyl cellulose (E465).

Other suitable gel materials for the gel ribbon include pectin, polyethylene oxide, polyvinyl alcohol, alginate, polycaprolactone, and gelatinised starch-based materials. The gel ribbons may be coated with gum arabic, pectin, alginate, or sodium alginate to modify their properties. For example, gum arabic, pectin and alginate all have a slight retarding effect on gel solubility of the gel ribbon (i.e., capsule shell), the extent of the effect varying according to coating thickness. Further, both pectin and alginate can be cross-linked, e.g., with calcium, to make the gel ribbon (i.e., capsule shell) pH sensitive such that it will not dissolve in the mouth but will dissolve in the stomach where pH is lower. More examples of suitable gel materials and coating materials are given in WO 97/35537 and WO 00/27367, the disclosures of which are incorporated herein by reference in their entireties.

In some aspects, any materials suitable for making films that can be sealed by a rotary process may be used in the present invention.

The die 10, 100, 200 of this disclosure is suitable to make softgel capsules with two or more incompatible pharmaceutical formulations. The active ingredients in the pharmaceutical formulations may be incompatible with each other, or the active ingredient of one formulation may be incompatible with an excipient in another formulation, or the pharmaceutical formulations may have excipients not compatible with each other. Encapsulating the two or more pharmaceutical formulations in separate chambers 14', 16' enables delivery of the pharmaceutical formulations in the same softgel capsules.

The multi-chamber softgel capsules with two or more pharmaceutical formulations can deliver combined or even synergistic therapeutic effects. The separation of the pharmaceutical formulations provides much needed flexibility in formulating wide range of active ingredients, regardless their compatibility. Further, incompatible excipients may be used in the same softgel capsules. This also provides the ability to encapsulating pharmaceutical formulations with different release profiles in the same softgel capsule. For example, one pharmaceutical formulation in one chamber 14' of the softgel capsule may be an immediate release formulation while the pharmaceutical formulation in the other chamber 16' of the same softgel capsule may be a delayed release formulation.

In some aspects, the multi-chamber softgel capsules allow half-dosing, which is a significant demand in animal health care, since animals can vary dramatically in size. For example, dogs can weigh over one hundred pounds, or as little as a few pounds, and half-dosing, or even quarter-dosing is possible with the multi-chamber softgel capsule produced by the die 10, 100, 200 of this disclosure.

Besides pharmaceutical formulations, the dies 10, 100, 200 of this disclosure are also suitable for producing multi-chamber softgel capsules containing two or more cosmetic products for a single use. The encapsulated cosmetic products may be in lotion, cream or paste forms. These products may either be anhydrous, aqueous or in emulsion form. The emulsion form may be either oil-in-water or water-in-oil emulsions.

The cosmetic products generally contain a vehicle or a carrier which is inert, and an active or performance ingredient. The amount of vehicle may range from about 5 to about 99%, or from about 25 to about 80% by weight of the total fill materials.

Various types of active ingredients may be present in cosmetic products. Active ingredients are defined as skin or hair benefit agents other than emollients and other than ingredients that merely improve the physical characteristics of the fill materials. Non-limiting examples of active ingredients in cosmetic products include sunscreens, tanning agents, skin anti-wrinkling agents, antidandruff agents, anti-acne agents, and hair growth stimulants.

Sunscreens include those materials commonly employed to block ultraviolet light. Exemplary compounds include derivatives of 4-aminobenzoic acid (PABA), cinnamate and salicylate. Some examples of octyl methoxycinnamate and 2-hydroxy-4-methoxy benzophenone (also known as oxybenzone) can be used. The exact amount of sunscreen employed in a sunscreen product can vary depending upon the degree of protection desired from the sun's UV radiation.

Tanning agents are materials that are capable of coloring the skin through chemical reaction; in particular, darkening the skin so that it resembles the darkening effect achieved by exposure of one's skin to the sun's rays (i.e., a natural tan). Some examples of tanning agents include dihydroxyacetone (DHA), erythrulose, and derivatives thereof. Similarly, imidazole and imidazole derivatives may be preferred and can also be used.

Anti-wrinkling agents may be the 2-hydroxyalkanoic acids, prostaglandins, retinoic acids, ceramides, and their derivatives.

Antidandruff agents are chemicals that are effective in the treatment of dandruff and/or the symptoms associated therewith. Antidandruff agents are well known in the art (see for example, U.S. 2004/0202636 (in particular, paragraphs 0041-0053); U.S. 2003/0003070 (in particular, paragraph 007); and U.S. Pat. No. 6,284,234 (in particular, column 13, lines 14-33). Exemplary antidandruff agents include, but are not limited to pyridinethione salts, such as calcium, magnesium, barium, strontium, zinc, and zirconium pyridinethione salts; azoles, such as climbazole, ketoconazole, and itraconazole; piroctone olamine (octopirox); undecylenic acid; undecylenamidopropylbetaine; coal tar (Neutrogena T/gel); salisylic acid (Ionil T); selenium sulfide (Selsun Blue); tea tree oil, and mixtures thereof.

Anti-acne agents are any chemical and/or biological agents (i.e. an antimicrobial peptide) that when topically administered at the site of acne, leads to a visible reduction of symptoms associated with the epithelial condition of acne vulgaris. Exemplary anti-acne agents include salicylic acid, sulfur, glycolic, pyruvic acid, resorcinol, N-acetylcysteine, picolinic acid, picolinic acid derivatives, picolinic acid analogs, benzoyl peroxide, and retinoids such as retinoic acid and its derivatives (e.g., cis and trans, esters).

Hair growth stimulants may include benzalkonium chlonde, benzethomum chlonde, phenol, estradiol, diphenhydramme hydrochloride, chlorpheniramme maleate, chlorophylhn derivatives, cholesterol, salicylic acid, cysteme, methionme, red pepper tincture, benzyl mcotmate, D, L-menthol, peppermint oil, calcium pantothenate, panthenol, castor oil, hmokitiol, prednisolone, resorcmol, monosacchandes and estenfied monosacchandes, chemical activators of protein kiase C enzymes, glycosammoglycan chain cellular uptake inhibitors, inhibitors of glycosidase activity, glycosarmnoglycanase inhibitors, esters of pyroglutamic acid, hexosaccharide acids or acylated hexosacchanc acids, aryl-substituted ethylenes, and N-acylated ammo acids.

Vitamins may also be included in the cosmetic products, such as vitamin A palmitate (retinyl palmitate) and vitamin E linoleate (tocopheryl linoleate). Other esters of vitamins A and E may also be utilized.

Many cosmetic products, especially those containing water, ideally include some protections against the growth of potentially harmful microorganisms, often by using preservatives. Suitable preservatives include alkyl esters of p-hydroxybenzoic acid, hydantoin derivatives, propionate salts, and a variety of quaternary ammonium compounds. Particularly preservatives are methyl paraben, propyl paraben, imidazolidinyl urea, sodium dehydroxyacetate, and benzyl alcohol.

Powders may be incorporated into the cosmetic products encapsulated in the multi-chamber softgels. Exemplary powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate, and mixtures thereof.

In some other aspects, the die 10 of this disclosure may be used to produce multi-chamber softgel capsules containing a pharmaceutical formulation and a dietary supplement, or two different dietary supplements, or different epoxy systems, or different multicomponent polyurethane systems. The dietary supplements may be vitamins, minerals, fibers, fatty acids, proteins, amino acids, herbals, and bodybuilding supplements. Specific examples of dietary supplements include iron, sodium, calcium, magnesium, carbohydrates, proteins, sugars (glucose), zinc, molybdenum, copper, potassium, manganese, chlorides, bicarbonate and carbonate, aluminum, arsenic, bromine, cadmium, chromium, chlorine, cobalt, fluorine, iodine, manganese, molybdenum nickel, phosphorus, selenium, silicon, vanadium, zinc, amino acids, vitamin A, vitamin D, vitamin E, vitamin K, vitamin C, vitamin B complex, thiamine (vitamin 31), riboflavin (vitamin 132). niacin (vitamin b3), pyridoxine (vitamin B6), biotin, pantothenic acid and pantethine, folic acid, vitamin B12, "unofficial" B vitamins including choline and inositol, vitamin P (bioflavonoids), and other vital nutrients, in addition to various homeopathic/alternative substances.

The epoxy systems encapsulated in different chambers may be used in industry applications, where the epoxy systems are mixed and reaction will occur to produce a desired product. For instance, two part epoxy systems could be included in the multi-chamber softgel capsule by incorporating an epoxy resin in one chamber and a hardener or curing agent in a second chamber.

In some embodiments, the epoxy resin comprises a curable epoxide, such as liquid polyglycidyl ethers of polyhydric phenols. In certain embodiments, epoxy resins include both monoepoxides and polyepoxides. Examples of monoepoxides include propylene oxide, allyl glycidyl ether, phenyl glycidyl ether, pentachlorophenyl glycidyl ether, tetrabromophenyl glycidyl ether and glycidyl methacrylate. The polyepoxides may have an average of more than 1.0 1,2-epoxy groups per average molecular weight. Among the polyepoxides which can be used herein are the polyglycidyl ethers of polyphenols, such as Bisphenol A. These may be attained, for example, by etherification of a polyphenol with epichlorohydrin or dichlorohydrin in the presence of an alkali. The phenolic compound may be 2,2-bis(4-hydroxyphenyl)propane, 4,4'-dihydroxybenzophenone, 1,1-bis(4-hydroxyphenyl)ethane, 2,2-bis(4-hydroxy-tertiarybutylphenyl)propane, bis(2-hydroxynaphthyl)methane or 1,5-dihydroxynaphthalene. The polyphenol can also be a novolak resin.

In some embodiments, the hardener or curing agent is an amine based hardener or curing agent, which are compounds having a primary or secondary amino functional group. Examples of suitable curing agents include diethylenetriamine, triethylenetetramine, isophoronediamine, diaminodiphenylmethane, diaminodiphenylsulfone, polyamides, dicyandiamide, hexahydrophthalic anhydride, methyltetrahydrophthalic anhydride, methyl nadic anhydride, tertiary amines, imidazoles, and amine complexes of boron trifluoride.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

The following examples are illustrative, but not limiting, of soft gel-mass capsules made by a process in accordance with the present disclosure. Other suitable modifications and adaptations of the variety of conditions and parameters normally encountered in the field, and which are obvious to those skilled in the art, are within the scope of the disclosure.

EXAMPLES

Example 1

The die 10 of FIG. 5 was made and used to produce two-chamber soft gelatin capsules encapsulating Peg 400/Peg 400 combo formulations, with each formulation having visual separation two fill materials (FIG. 16). The hydrophilic/lipophilic softgel capsules were produced with no issues. The softgel capsules were dried for at about 4 days and both sides of the capsules had a hardness value in the 9N range. No appearance issues have been identified for the softgel capsules after the drying. For example, no leaking was observed for the softgel capsules. Also no leaking between chambers occurred, verifying the barrier seal performed as expected. Overall the softgel capsules had all the normal properties of a "regularly" produced softgel capsule.

Example 2

The die 10 was used to produce two-chamber softgel capsules with one chamber 14', 16' containing a liquid formulation of Labrasol® (surfactant) and the other chamber 14', 16' containing a semi-solid formulation of Gelucire®. The encapsulating of the two formulations using the die 10 was successful with no issues noticed. This example shows an advantage of being able to form gelatin softgel encapsulation with liquid and semi-solid formulations in separate chambers of the same capsules. The successful encapsulation of the two formulations suggested that any combination of active ingredients or excipients can be encapsulated into a multi-chamber softgel capsule using the die 10 of this disclosure, examples including dietary, nutritional, animal health, cosmetic products.

Example 3

The die 100 of FIG. 10 was made and used to produce softgel capsules with a twist-off cap 25' for use in the cosmetic industry. The softgel capsules were successfully produced (FIG. 17). The twist-off cap 25' and application of the contents in the two chambers 14', 16' were tested (FIG. 18). The die 100 of this disclosure met the demands of cosmetic industry for producing single-use softgel capsules containing two or more cosmetic products.

Example 4

The die 100 of the present invention is used to make softgel capsules with two chambers, encapsulating retinol and vitamin C respectively. Retinol and vitamin C are known incompatible ingredients.

What is claimed is:
1. A die for a multi-chamber softgel capsule, the die comprising:
a die pocket defined by a die pocket wall and a bottom surface; and
one or more partitioning walls dividing the die pocket into two or more chambers, wherein
the die pocket wall and the one or more partitioning walls have their respective top sections defined as lands,
a top of the land of the perimeter of the die pocket wall is in a plane,
a lowest point of the top of the land of the one or more partitioning walls is lower than the plane by a gap;
at least one of the one or more partitioning walls has a recess in the top of its land; and
a size of the gap is less than a thickness of one gel ribbon used to make the softgel capsule such that two gel ribbons used to make the softgel capsule are pressed tightly together by the tops of the lands of the partitioning walls of the pair of mated dies.
2. The die of claim 1, wherein the top of at least one of the lands has a shape selected from flat, round, curved, plateaued, and angled.
3. The die of claim 1, further comprising at least one air hole in each chamber.
4. The die of claim 1, wherein the one or more partitioning walls are perpendicular to the plane.
5. The die of claim 1, further comprising a twist-off cap.
6. The die of claim 5, further comprising one discharge channel in fluid connection with each chamber.
7. The die of claim 6, wherein the discharge channels are separated from the twist-off cap by a channel wall.
8. The die of claim 7, wherein a height of the channel wall is lower than a height of a highest point of the die pocket wall, and is higher than a height of the one or more partitioning walls.
9. The die of claim 1, wherein each said one or more partitioning walls has a shape selected from a straight line and a curved line when viewed from above the die.
10. The die of claim 1, having two or more partitioning walls configured in parallel to one another.
11. The die of claim 1, having two or more partitioning walls that intersect with each other to form four or more chambers.

12. The die of claim 1, wherein the one or more partitioning walls have a thickness of from about 0.254 mm to about 2.54 mm.

13. The die of claim 1, wherein at least one of the one or more partitioning walls has a thickness that decreases from a portion proximate to the bottom surface to the land of the at least one partitioning wall.

14. The die of claim 1, including a plurality of partitioning walls that intersect to form a shape of a star or a grid when viewed from above.

15. The die of claim 1, wherein a size of the gap is in a range of from about 0.254 mm to about 2.54 mm and the gap is less than about 95% of a thickness of a gel ribbon suitable to be used with the die.

16. The die of claim 1, wherein the die pocket has the shape of a half or portion of one of a sphere, an oval, a cuboid, a cube, a rounded cuboid, a rounded cube, a heart, a water drop, a fish, a bear, or a pear.

17. The die of claim 1, wherein the die pocket has the shape of one of a cone or pyramid, and the pyramid is selected from three-sided, four-sided, five-sided, six-sided, eight-sided and ten-sided pyramids.

18. The die of claim 1, wherein at least one of the two or more chambers has a different size than another of the two or more chambers.

19. The die of claim 1, wherein the top of the land of the partitioning wall has a recess that is a crescent shape as viewed in a side view.

20. A die roll having a surface comprising a plurality of the dies of claim 1.

21. The die roll of claim 20, wherein the plurality of the dies are arranged in from about 5 to 30 rows on the surface.

22. A rotary-die encapsulation machine comprising at least one die roll of claim 20.

23. A multi-chamber softgel capsule produced using the die of claim 1, wherein the multi-chamber softgel capsule has two or more chambers separated by one or more barrier seals.

24. A pair of mated dies for producing a multi-chamber softgel capsule, wherein each of the pair of mated dies comprises:
 a die pocket defined by a die pocket wall and a bottom surface; and
 one or more partitioning walls dividing the die pocket into two or more chambers,
 wherein the die pocket wall and the one or more partitioning walls have their respective top sections defined as lands,
 the partitioning walls of the pair of mated dies have heights such that there is a gap between a top of the land of one said partitioning wall of one of the dies and the top of the land of at least one of the partitioning walls of the other die;
 at least one of the one or more partitioning walls has a recess in the top of its land; and
 a size of the gap is less than a thickness of one gel ribbon used to make the softgel capsule such that two gel ribbons used to make the softgel capsule are pressed tightly together by the tops of the lands of the partitioning walls of the pair of mated dies.

25. The pair of mated dies of claim 24, wherein a size of the gap between the top of the land of the partitioning walls of the pair of mated dies is in a range from about 0.508 mm to about 5.08 mm and the gap between the top of the land of the partitioning walls of the pair of mated dies is less than about 95% of a total thickness of a gel ribbon located between the pair of mated dies.

* * * * *